United States Patent
Fernandez Forner et al.

(10) Patent No.: US 7,358,260 B2
(45) Date of Patent: *Apr. 15, 2008

(54) QUINUCLIDINE DERIVATIVES AND MEDICINAL COMPOSITIONS CONTAINING THE SAME

(75) Inventors: María Dolors Fernandez Forner, Barcelona (ES); María Prat Quiñones, Barcelona (ES); María Antonia Buil Albero, Barcelona (ES)

(73) Assignee: Laboratories Almirall, S.A., Barcelona (ES)

( * ) Notice: Subject to any disclaimer, the term of this patent is extended or adjusted under 35 U.S.C. 154(b) by 0 days.

This patent is subject to a terminal disclaimer.

(21) Appl. No.: 11/636,181

(22) Filed: Dec. 8, 2006

(65) Prior Publication Data

US 2007/0099953 A1    May 3, 2007

Related U.S. Application Data

(60) Continuation of application No. 11/325,059, filed on Jan. 3, 2006, now Pat. No. 7,196,098, which is a division of application No. 11/116,777, filed on Apr. 28, 2005, now Pat. No. 7,078,412, which is a continuation of application No. 10/740,264, filed on Dec. 17, 2003, now Pat. No. 7,109,210, which is a division of application No. 10/047,464, filed on Jan. 14, 2002, now Pat. No. 6,750,226, which is a continuation of application No. PCT/EP00/06469, filed on Jul. 7, 2000.

(30) Foreign Application Priority Data

Jul. 14, 1999   (ES) ................................ 9901580

(51) Int. Cl.
*A61K 31/439* (2006.01)
*C07D 453/02* (2006.01)

(52) U.S. Cl. .................. 514/305; 546/137; 514/826

(58) Field of Classification Search ................ 514/305, 514/826; 546/137
See application file for complete search history.

(56) References Cited

U.S. PATENT DOCUMENTS 6,750,226 B2 * 6/2004 Forner et al. ................ 514/305
7,109,210 B2 * 9/2006 Fernandez Forner et al. .......................... 514/305

* cited by examiner

*Primary Examiner*—Charanjit S. Aulakh
(74) *Attorney, Agent, or Firm*—Hoxie & Associates LLC

(57) ABSTRACT

The invention provides 1-phenethyl-3 (R)-(9[H]-xanthene-9-carbonyloxy)-1-azoniabicyclo[2.2.2]octane in salt form, pharmaceutical compositions comprising it, and methods of using it for treatment of respiratory disorders.

6 Claims, No Drawings

QUINUCLIDINE DERIVATIVES AND MEDICINAL COMPOSITIONS CONTAINING THE SAME

CROSS-REFERENCE TO RELATED APPLICATIONS

This application is a continuation of U.S. patent application Ser. No. 11/325,059, filed Jan. 3, 2006, now U.S. Pat. 7,196,098 which is a divisional of U.S. patent application Ser. No. 11/116,777, filed Apr. 28, 2005 (now U.S. Pat. No. 7,078,412), which is a continuation of U.S. patent application Ser. No. 10/740,264, filed Dec. 17, 2003 (now U.S. Pat. No. 7,109,210), which is a divisional of U.S. patent application Ser. No. 10/047,464, filed Jan. 14, 2002 (now U.S. Pat. No. 6,750,226), which is a continuation of International Application No. PCT/EP00/06469, filed Jul. 7, 2000, and published in English on Jan. 18, 2001, which claims the benefit of Spanish Application No. P9901580, filed Jul. 14, 1999, the contents of each of which are incorporated herein by reference.

The novel structures according to the invention are antimuscarinic agents with a potent and long lasting effect. In particular, these compounds show high affinity for muscarinic $M_3$ receptors(Hm3).

In accordance with their nature as $M_3$ antagonists, the new compounds are suitable for treating the following diseases: respiratory disorders such as chronic obstructive pulmonary disease(COPD), chronic bronchitis, bronchial hyperreactivity, asthma and rhinitis; urological disorders such as urinary incontinence, pollakinuria in neuripenia pollakinuria, neurogenic or unstable bladder, cystospasm and chronic cystitis; and gastrointestinal disorders such as irritable bowel syndrome, spastic colitis, diverticulitis and peptic ulceration.

The compounds claimed are also useful for the treatment of the respiratory diseases detailed above in association with $\beta_2$ agonists, steroids, antiallergic drugs or phosphodiesterase IV inhibitors.

Compounds of the present invention may also be expected to have anti-tussive properties.

Depending on their nature the new compounds may be suitable for treating vagally induced sinus bradycardia.

Compounds with related structures have been described as anti-spasmodics and anti-cholinergic agents in several patents.

For example, in patent FR 2012964 are described quinuclidinol derivatives of the formula:

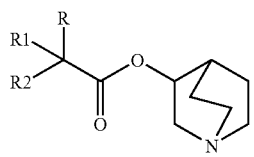

in which R is H, OH or an alkyl group having 1 to 4 carbon atoms; $R_1$ is a phenyl or thienyl group; and $R_2$ is a cyclohexyl, cyclopentyl or thienyl group, or, when R is H, $R_1$ and $R_2$ together with the carbon atom to which they are attached, form a tricyclic group of the formula:

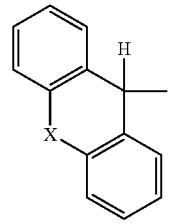

in which X is —O—, —S— or —$CH_2$—, or an acid addition or quaternary ammonium salt thereof.

EP-418716 describes thienyl carboxylate esters of formula

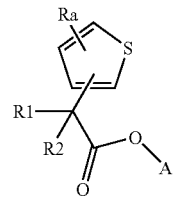

wherein A is a group

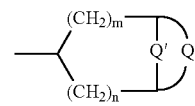

m and n=1 or 2

Q is a —$CH_2$—$CH_2$—, —$CH_2$—$CH_2$—$CH_2$—, —CH=CH—, group

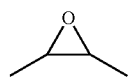

Q' is a =NR or NRR= group; $R_1$ is a thienyl, phenyl, furyl, cyclopentyl or cyclohexyl group, optionally substituted; $R_2$ is H, OH, $C_1$-$C_4$ alkoxy or $C_1$-$C_4$ alkyl and $R_a$ is H, F, Cl, $CH_3$— or —NR.

U.S. Pat. No. 5,654,314 describes compounds of formula:

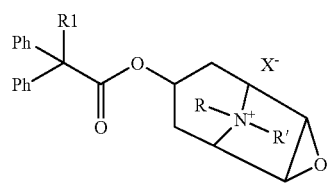

wherein R is an optionally halo- or hydroxy-substituted $C_{1-4}$ alkyl group; R is a $C_{1-4}$ alkyl group; or R and R= together form a $C_{4-6}$ alkylene group; $X^-$ is an anion; and $R_1$ is H, OH, —$CH_2OH$, $C_{1-4}$ alkyl or $C_{1-4}$ alkoxy.

The present invention provides new quinuclidine derivatives with potent antagonist activity at muscarinic M₃ receptors which have the chemical structure described in formula (I):

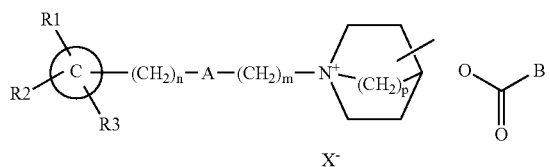

wherein:

Ĉ is a phenyl ring, a $C_4$ to $C_9$ heteroaromatic group containing one or more heteroatoms (preferably selected from nitrogen, oxygen and sulphur atoms), or a naphthalenyl, 5,6,7,8-tetrahydronaphthalenyl or biphenyl group;

$R^1$, $R^2$ and $R^3$ each independently represent a hydrogen or halogen atom, or a hydroxy group, or a phenyl, —$OR^4$, —$SR^4$, —$NR^4R^5$, —$NHCOR^4$, —$CONR^4R^5$, —CN, —$NO_2$, —$COOR^4$ or —$CF_3$ group, or a straight or branched lower alkyl group which may optionally be substituted, for example, with a hydroxy or alkoxy group, wherein $R^4$ and $R^5$ each independently represent a hydrogen atom, straight or branched lower alkyl group, or together form an alicyclic ring; or $R^1$ and $R^2$ together form an aromatic, alicyclic or heterocyclic ring;

n is an integer from 0 to 4;

A represents a —$CH_2$—, —CH=$CR^6$—, —$CR^6$=CH—, —$CR^6R^7$—, —CO—, —O—, —S—, —S(O)—, $SO_2$ or —$NR^6$— group, wherein $R^6$ and $R^7$ each independently represent a hydrogen atom, straight or branched lower alkyl group, or $R^6$ and $R^7$ together form an alicyclic ring;

m is an integer from 0 to 8; provided that when m=0, A is not —$CH_2$—;

p is an integer from 1 to 2 and the substitution in the azoniabicyclic ring may be in the 2, 3 or 4 position including all possible configurations of the asymmetric carbons;

B represents a group of formula i) or ii):

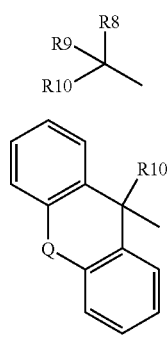

wherein $R^{10}$ represents a hydrogen atom, a hydroxy or methyl group; and $R^8$ and $R^9$ each independently represents

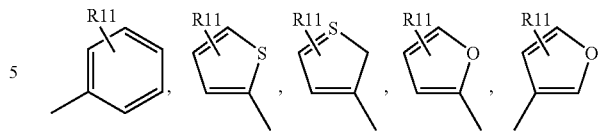

wherein $R^{11}$ represents a hydrogen or halogen atom, or a straight or branched lower alkyl group and Q represents a single bond, —$CH_2$—, —$CH_2$—$CH_2$—, —O—, —O—$CH_2$—, —S—, —S—$CH_2$— or —CH=CH—; and when i) or ii) contain a chiral centre they may represent either configuration; X represents a pharmaceutically acceptable anion of a mono or polyvalent acid.

In the quaternary ammonium compounds of the present invention represented by formula (I) an equivalent of an anion (X⁻) is associated with the positive charge of the N atom. X⁻ may be an anion of various mineral acids such as, for example, chloride, bromide, iodide, sulfate, nitrate, phosphate, and organic acids such as, for example, acetate, maleate, fumarate, citrate, oxalate, succinate, tartrate, malate, mandelate, methanesulfonate and p-toluenesulfonate. X⁻ is preferably an anion selected from chloride, bromide, iodide, sulphate, nitrate, acetate, maleate, oxalate or succinate. More preferably X⁻ is chloride, bromide or trifluoroacetate.

The compounds of the present invention represented by the formula (I) described above, which may have one or more assymetric carbons, include all the possible stereoisomers. The single isomers and mixtures of the isomers fall within the scope of the present invention.

If any of $R^1$ to $R^7$ or $R^{11}$ represents an alkyl group, it is preferred that said alkyl group contains 1 to 8, preferably 1 to 6 and more preferably 1 to 4 carbon atoms. In particular it is preferred that any alkyl group is represented by a methyl, ethyl, propyl, including i-propyl, butyl including a n-butyl, sec-butyl and tert-butyl.

The alicyclic and heterocyclic rings mentioned in relation to formula (I) preferably comprise from 3 to 10, preferably from 5 to 7 members. The aromatic rings mentioned in relation to formula (I) above preferably contain from 6 to 14, preferably 6 or 10 members.

Preferred compounds of formula (I) are those wherein Ĉ represents a phenyl, pyrrolyl, thienyl, furyl, biphenyl, naphthalenyl, 5,6,7,8-tetrahydronaphthalenyl, benzo[1,3]dioxolyl, imidazolyl or benzothiazolyl group, in particular a phenyl, pyrrolyl, or thienyl group; $R^1$, $R^2$ and $R^3$ each independently represent a hydrogen or halogen atom, or a hydroxyl, methyl, tert-butyl, —$CH_2OH$, 3-hydroxypropyl, —OMe, —$NMe_2$, —NHCOMe, —$CONH_2$, —CN, —$NO_2$, —COOMe or —$CF_3$ group, in particular a hydrogen atom, a hydroxy group or a halogen atom, wherein the halogen atom is preferably fluorine; n=0 or 1; m is an integer from 1 to 6, particularly 1, 2 or 3; A represents a —$CH_2$—, —CH=CH—, —CO—, —NH—, —NMe-, —O— or —S— group, in particular a —$CH_2$—, —CH=CH— or —O— group.

It is also preferred that p=2 and the substituent group —OC(O)B attached to the azoniabicyclo[2.2.2]octane is at the 3 position, preferably having the (R) configuration.

Further preferred compounds of formula I are those wherein B is a group of formula i) or ii) as defined above wherein, if B is a group of formula (i), $R^8$ and $R^9$ each independently represent a phenyl, 2-thienyl, 3-thienyl, 2-furyl or 3-furyl group, wherein $R^{11}$ is hydrogen atom; and, if B is a group of formula (ii), Q represents a single bond, —CH$_2$—, —CH$_2$—CH$_2$—, —O— or —S— group, in particular a single bond, —CH$_2$—, —CH$_2$—CH$_2$— or —O— group, most preferably a single bond or —O— group; and in any case R$^{10}$ is a hydrogen atom or a hydroxy or methyl group; and when i) or ii) contain a chiral centre they may represent either the (R) or the (S) configuration.

Most preferably the —OC(O)B group in formula (I) is diphenylacetoxy, 2-hydroxy-2,2-diphenyl-acetoxy, 2,2-diphenylpropionyloxy, -hydroxy-2-phenyl-2-thien-2-yl-acetoxy, 2-furan-2-yl-2-hydroxy-2-phenylacetoxy, 2,2-dithien-2-ylacetoxy, 2-hydroxy-2,2-di-thien-2-ylacetoxy, 2-hydroxy-2,2-di-thien-3-ylacetoxy, 9-hydroxy-9[H]-fluorene-9-carbonyloxy, 9-methyl-9[H]-fluorene-9-carbonyloxy, 9[H]-xanthene-9-carbonyloxy, 9-hydroxy-9[H]-xanthene-9-carbonyloxy, 9-methyl-9[H]-xanthene-9-carbonyloxy, 2,2-bis(4-fluorophenyl)-2-hydroxyacetoxy, 2-hydroxy-2,2-di-p-tolylacetoxy, 2,2-difuran-2-yl-2-hydroxyacetoxy, 2,2-dithien-2-ylpropionyloxy, 9,10-dihydroanthracene-9-carbonyloxy, 9[H]-thioxanthene-9-carbonyloxy, or 5[H]-dibenzo[a,d]cycloheptene-5-carbonyloxy. Especially preferred compounds are those wherein the —OC(O)B group in formula (I) is diphenylacetoxy, 2-hydroxy-2,2-diphenyl-acetoxy, 2,2-diphenylpropionyloxy, 2-hydroxy-2-phenyl-2-thien-2-yl-acetoxy, 2-furan-2-yl-2-hydroxy-2-phenylacetoxy, 2,2-dithien-2-ylacetoxy, 2-hydroxy-2,2-di-thien-2-ylacetoxy, 2-hydroxy-2,2-di-thien-3-ylacetoxy, 9-hydroxy-9[H]-fluorene-9-carbonyloxy, 9-methyl-9[H]-fluorene-9-carbonyloxy, 9[H]-xanthene-9-carbonyloxy, 9-hydroxy-9[H]-xanthene-9-carbonyloxy or 9-methyl-9[H]-xanthene-9-carbonyloxy.

The most preferred compounds of formula (I) are those wherein the azoniabicyclo group is substituted on the nitrogen atom with a 3-phenoxypropyl, 2-phenoxyethyl, 3-phenylallyl, phenethyl, 4-phenylbutyl, 3-phenylpropyl, 3-[2-hydroxyphenyl]propyl, 3-[4-fluorophenoxy]propyl, 2-benzyloxyethyl, 3-pyrrol-1-ylpropyl, 2-thien-2-ylethyl, 3-thien-2-ylpropyl, 3-phenylaminopropyl, 3(methylphenylamino)propyl, 3-phenylsulfanylpropyl, 3-o-tolyloxypropyl, 3-(2,4,6-trimethylphenoxy)propyl, 3-(2-tert-butyl-6-methylphenoxy)propyl, 3-(biphenyl-4-yloxy)propyl, 3-(5,6,7,8-tetrahydronaphthalen-2-yloxy)-propyl, 3-(naphthalen-2-yloxy)propyl, 3-(naphthalen-1-yloxy)propyl, 3-(2-chlorophenoxy)propyl, 3-(2,4-difluorophenoxy)propyl, 3-(3-trifluoromethylphenoxy)propyl, 3-(3-cyanophenoxy)propyl, 3-(4-cyanophenoxy)propyl, 3-(3-methoxyphenoxy)propyl, 3-(4-methoxyphenoxy)propyl, 3-(benzo[1,3]dioxol-5-yloxy)propyl, 3-(2-carbamoylphenoxy)propyl, 3-(3-dimethylaminophenoxy)propyl, 3-(4-nitrophenoxy)propyl, 3-(3-nitrophenoxy)propyl, 3-(4-acetylaminophenoxy)propyl, 3-(3-methoxycarbonylphenoxy)propyl, 3-[4-(3-hydroxypropyl)phenoxy]propyl, 3-(2-hydroxymethylphenoxy)propyl, 3-(3-hydroxymethylphenoxy)propyl, 3-(4-hydroxymethylphenoxy)propyl, 3-(2-hydroxyphenoxy)propyl, 3-(4-hydroxyphenoxy)propyl, 3-(3-hydroxyphenoxy)propyl, 4-oxo-4-thien-2-ylbutyl, 3-(1-methyl-[1H]-imidazol-2-ylsulfanyl)propyl, 3-(benzothiazol-2-yloxy)propyl, 3-benzyloxypropyl, 6-(4-phenylbutoxy)hexyl, 4-phenoxybutyl, or 2-benzyloxyethyl group. Especially preferred compounds are those wherein the azoniabicyclo group is substituted on the nitrogen atom with a 3-phenoxypropyl, 2-phenoxyethyl, 3-phenylallyl, phenethyl, 4-phenylbutyl, 3-phenylpropyl, 3-[2-hydroxyphenoxy]propyl, 3-[4-fluorophenoxy]propyl, 2-benzyloxyethyl, 3-pyrrol-1-ylpropyl, 2-thien-2-ylethyl or 3-thien-2-ylpropyl group.

The following compounds are intended to illustrate but not to limit the scope of the present invention.

3(R)-Diphenylacetoxy-1-(3-phenoxy-propyl)-1-azoniabicyclo[2.2.2]octane; bromide

3(R)-(2-Hydroxy-2,2-diphenyl-acetoxy)-1-(3-phenoxypropyl)-1-azoniabicyclo[2.2.2]octane; bromide 3(R)-(2,2-Diphenylpropionyloxy)-1-(3-phenoxypropyl)-1-azoniabicyclo[2.2.2]octane; bromide 3(R)-(2-Hydroxy-2-phenyl-2-thien-2-yl-acetoxy)-1-(3-phenoxypropyl)-1-azonia-bicyclo[2.2.2]octane; bromide 3(R)-(2-Furan-2-yl-2-hydroxy-2-phenylacetoxy)-1-(3-phenylallyl)-1-azoniabicyclo[2.2.2]octane; bromide 3(R)-(2-Furan-2-yl-2-hydroxy-2-phenylacetoxy)-1-(2-phenoxyethyl)-1-azoniabicyclo[2.2.2]octane; bromide 3(R)-(2-Furan-2-yl-2-hydroxy-2-phenylacetoxy)-1-(3-phenoxypropyl)-1-azoniabicyclo[2.2.2]octane; bromide 3(R)-(2,2-Dithien-2-ylacetoxy)-1-(3-phenoxypropyl)-1-azonia-bicyclo[2.2.2]octane; bromide 3(R)-(2-Hydroxy-2,2-di-thien-2-ylacetoxy)-1-phenethyl-1-azoniabicyclo[2.2.2]octane; bromide 3(R)-(2-Hydroxy-2,2-di-thien-2-ylacetoxy)-1-(4-phenylbutyl)-1-azoniabicyclo[2.2.2]octane; bromide 3(R)-(2-Hydroxy-2,2-dithien-2-ylacetoxy)-1-(3-phenoxypropyl)-1-azonia-bicyclo[2.2.2]octane; bromide 1-[3-(4-Fluorophenoxy)propyl]-3(R)-(2-hydroxy-2,2-dithien-2-ylacetoxy)-1-azoniabicyclo-[2.2.2]octane; chloride 3(R)-(2-Hydroxy-2,2-dithien-2-ylacetoxy)-1-[3-(2-hydroxyphenoxy)propyl]-1-azoniabicyclo[2.2.2]octane; trifluoroacetate 3(R)-(2-Hydroxy-2,2-dithien-2-ylacetoxy)-1-(3-pyrrol-1-ylpropyl)-1-azonia-bicyclo[2.2.2]octane; trifluoroacetate 3(R)-(2-Hydroxy-2,2-dithien-2-ylacetoxy)-1-(2-thien-2-ylethyl)-1-azoniabicyclo[2.2.2]octane; bromide 3(R)-(2-Hydroxy-2,2-dithien-2-ylacetoxy)-1-(3-thien-2-ylpropyl)-1-azoniabicyclo[2.2.2]octane; bromide 1-(2-Benzyloxyethyl)-3(R)-(2-hydroxy-2,2-dithien-2-ylacetoxy)-1-azoniabicyclo[2.2.2]octane; trifluoroacetate 3(R)-(2-Hydroxy-2,2-dithien-3-ylacetoxy)-1-(3-phenoxypropyl)-1-azoniabicyclo[2.2.2]octane; bromide 1-(3-phenylallyl)-3(R)-(9-Hydroxy-9[H]-fluorene-9-carbonyloxy)-1-azoniabicyclo[2.2.2]octane; bromide 3(R)-(9-Hydroxy-9[H]-fluorene-9-carbonyloxy)-1-(3-phenoxypropyl)-1-azoniabicyclo[2.2.2]octane; bromide 3(R)-(9-Hydroxy-9[H]-fluorene-9-carbonyloxy)-1-phenethyl-1-azoniabicyclo[2.2.2]octane; bromide 3(R)-(9-Hydroxy-9H-fluorene-9-carbonyloxy)-1-(3-thien-2-ylpropyl)-1-azoniabicyclo[2.2.2]octane; bromide 3(R)-(9-Methyl-9[H]-fluorene-9-carbonyloxy)-1-(3-phenylallyl)-1-azoniabicyclo[2.2.2]octane; bromide 3(R)-(9-Methyl-9[H]-fluorene-9-carbonyloxy)-1-(3-phenoxypropyl)-1-azoniabicyclo[2.2.2]octane; bromide 1-(4-Phenylbutyl)-3(R)-(9[H]-xanthene-9-carbonyloxy)-1-azoniabicyclo[2.2.2]octane; bromide 1-(2-Phenoxyethyl)-3(R)-(9[H]-xanthene-9-carbonyloxy)-1-azoniabicyclo[2.2.2]octane; bromide 1-(3-Phenoxypropyl)-3(R)-(9[H]-xanthene-9-carbonyloxy)-1-azoniabicyclo[2.2.2]octane; bromide 1-Phenethyl-3(R)-(9[H]-xanthene-9-carbonyloxy)-1-azoniabicyclo[2.2.2]octane; bromide 3(R)-(9-Hydroxy-9[H]-xanthene-9-carbonyloxy)-1-(3-phenoxypropyl)-1-azoniabicyclo[2.2.2]octane; bromide 3(R)-(9-Hydroxy-9[H]-xanthene-9-carbonyloxy)-1-phenethyl-1-azoniabicyclo[2.2.2]octane; bromide 3(R)-(9-Hydroxy-9H-xanthene-9-carbonyloxy)-1-(3-thien-2-ylpropyl)-1-azoniabicyclo[2.2.2]octane; bromide 3(R)-(9-Methyl-9[H]-xanthene-9-carbonyloxy)-1-(3-phenoxy-propyl)-1-azonia-bicyclo[2.2.2]octane; bromide The present invention also provides processes for preparing compounds of formula (I).

The quaternary ammonium derivatives of general Formula I, may be prepared by reaction of an alkylating agent of general Formula II with compounds of general Formula III. In Formulas I, II and III, $R^1$, $R^2$, $R^3$, $\hat{C}$, A, X, B, n, m and p are as defined above.

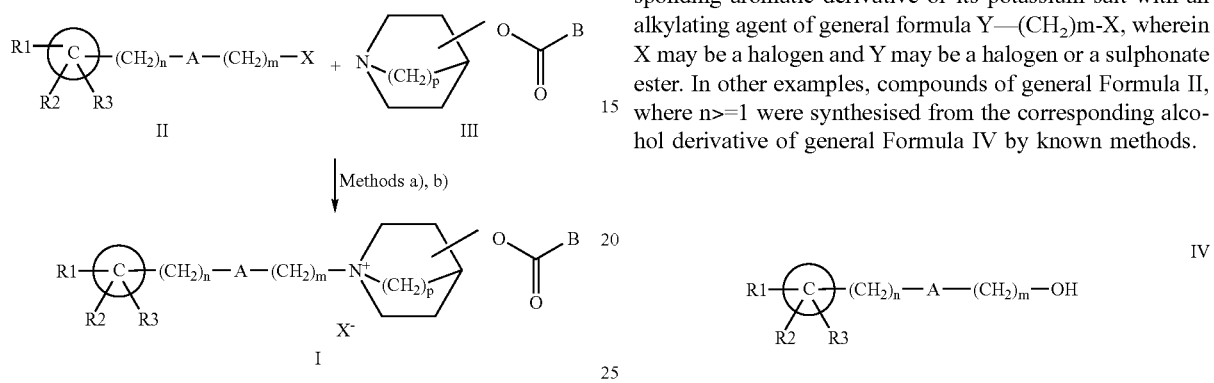

This alkylation reaction may be carried out by two different experimental procedures, a) and b) which are described below. In particular method b) provides a new experimental process, using solid phase extraction methodologies, that allows the parallel preparation of several compounds. Methods a) and b) are described in the experimental section. Compounds of general Formula II which are not commercially available have been prepared by synthesis according to standard methods. For example, compounds wherein n=0 and A=—O—, —S— or —NR$^6$, wherein R$^6$ is as defined above, were obtained by reaction of the corresponding aromatic derivative or its potassium salt with an alkylating agent of general formula Y—(CH$_2$)m-X, wherein X may be a halogen and Y may be a halogen or a sulphonate ester. In other examples, compounds of general Formula II, where n>=1 were synthesised from the corresponding alcohol derivative of general Formula IV by known methods.

IV

Compounds of general Formula III may be prepared by three different methods c, d and e illustrated in the following scheme and detailed in the experimental section.

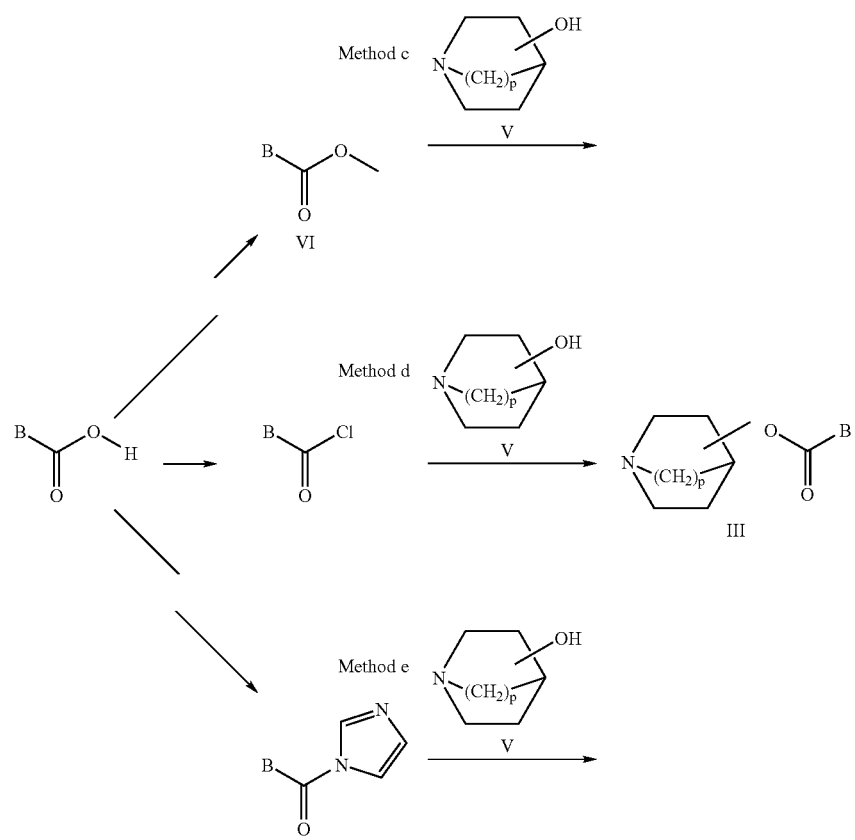

Some compounds of general formula III where B is a group of formula i), $R^8$ and $R^9$ are as described above and $R^{10}$ is a hydroxy group, may also be prepared from the glyoxalate esters of general formula VII by reaction with the corresponding organometallic derivative.

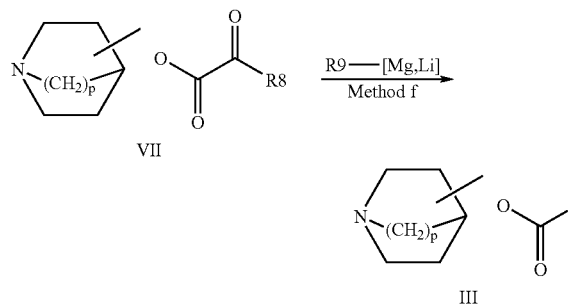

VII

III

Compounds of general formula VII may be prepared from the corresponding glyoxylic acids following the standard methods c, d and e described above and detailed in the experimental section. The glyoxalate derivatives of formula VII where $R^8$ is a 2-thienyl or 2-furyl group have not been described before.

The following compounds are examples of compounds of general formula III and VII which have not been described before:

9-Methyl-9[H]-fluorene-9-carboxylic acid 1-azabicyclo[2.2.2]oct-3(R)-yl ester (intermediate I-1c).;

9-Methyl-9[H]-xanthene-9-carboxylic acid 1-azabicyclo[2.2.2]oct-3(R)-yl ester (intermediate I-1d);

2-Hydroxydithien-2-yl-acetic acid 1-azabicyclo[2.2.2]oct-4-yl ester (intermediate I-4a).

Oxothien-2-yl-acetic acid 1-azabicyclo[2.2.2]oct-4-yl ester (intermediate I-4b).

Oxothien-2-yl-acetic acid 1-azabicyclo[2.2.2]oct-3(R)-yl ester (intermediate I-4g).

Oxofuran-2-yl-acetic acid 1-azabicyclo[2.2.2]oct-3(R)-yl ester (intermediate I-4e).

2-Hydroxy-2,2-difuran-2-yl-acetic acid 1-azabicyclo[2.2.2]oct-3(R)-yl ester (intermediate I-4d).

Compounds of Formula V could be:

4-hydroxy-1-azabicyclo[2.2.1]heptane, described in WO150080

4-hydroxy-1-azabicyclo[2.2.2]octane, described in Grob, C. A. et.al. Helv. Chim. Acta (1958), 41, 1184-1190

3(R)-hydroxy-1-azabicyclo[2.2.2]octane or 3(S)-hydroxy-1-azabicyclo[2.2.2]octane, described in Ringdahl, R. Acta Pharm Suec. (1979), 16, 281-283 and commercially available from CU Chemie Uetikon GmbH.

The following examples are intended to illustrate, but not to limit, the experimental procedures that have been described above.

The structures of the prepared compounds were confirmed by $^1$HNMR and MS. The NMR were recorded using a Varian 300 MHz instrument and chemical shifts are expressed as parts per million (δ) from the internal reference tetramethyl silane. Their purity was determined by HPLC, using reverse phase chromatography on a Waters instrument, with values greater than 95% being obtained. Molecular ions were obtained by electrospray ionization mass spectometry on a Hewlett Packard instrument.

Method - a -

EXAMPLE 20

Preparation of 3(R)-(2-Furan-2-yl-2-hydroxy-2-phenyl acetoxy)-1-(3-phenoxypropyl)-1-azoniabicyclo[2.2.2]octane, bromide 200 mg of (Furan-2-yl)-hydroxy-phenylacetic acid 1-azabicyclo[2.2.2]oct-3(R)-yl ester (0.6 mmol) were suspended in 4 ml of CH3CN and 6 ml of CHCl3. To this suspension were added 0.48 ml (3 mmol) of 3-phenoxypropyl bromide. After stirring for 72 h at room temperature in inert atmosphere, solvents were evaporated. Ether was added and the mixture stirred. The solid obtained was filtered and washed several times with ether. The yield was 0.27 g (83%) of title compound as a mixture of diastereomers.

$^1$H-NMR (DMSO-d6): δ 1.50-2.20 (m, 6H), 2.25 (m, 1H), 3.10 (m, 1H), 3.20-3.60 (m, 6H), 3.95 (m, 1H), 4.05 (m, 2H), 5.20 (m, 1H), 6.25-6.35 (double dd, 1H), 6.45 (m, 1H), 6.95 (m, 4H), 7.30-7.50 (m, 7H), 7.70 (m, 1H); MS [M-Br]$^+$: 462; mp 166° C.

Method - b -

EXAMPLE 51

Preparation of 3(R)-(2-Hydroxy-2,2-di-thien-2-yl acetoxy)-1-[3-(naphthalen-1-yloxy)propyl]-1-azoniabicyclo[2.2.2]octane; trifluoroacetate 60 mg (0.17 mmols) of hydroxy-dithien-2-yl-acetic acid 1-aza-bicyclo[2.2.2]oct-3(R)-yl ester were dissolved in 1 ml of dmso. To this solution 188 mg (0.85 mmol) of 3-(naphthalen-1-yloxy)-propyl chloride were added. After stirring overnight at room temperature, the mixture was purified by solid phase extraction with a cation exchange Mega Bond Elut cartridge, previously conditioned at pH=7.5 with 0.1 M NaH2PO4 buffer. The reaction mixture was applied to the cartridge and washed first with 2 ml of DMSO and then three times with 5 ml of CH3CN, rinsing away all starting materials. The ammonium derivative was eluted with 5 ml of 0.03 M TFA solution in CH3CN:CHCl3 (2:1). This solution was neutralized with 300 mg of poly(4-vinylpyridine), filtered and evaporated to dryness.

The yield was 17 mg (15%) of title compound. $^1$H-NMR (DMSO-d6): δ 1.7-2.1 (m, 4H), 2.2-2.4 (m, 3H), 3.2-3.6 (m, 7H), 4.0 (m, 1H), 4.2 (t, 2H), 5.25 (m, 1H), 7.0 (m 3H), 7.2 (m, 2H), 7.4-7.6 (m, 7H), 7.85 (d, 1H), 8.2 (d, 1H); MS [M-CF$_3$COO]$^+$: 534.

Method - c -

Methyl ester derivatives of general Formula VI were prepared by standard methods of esterification from the corresponding carboxylic acid or following the procedures described in examples I-1e, I-1f and I-1g or according to procedures described in literature: FR 2012964; Larsson. L et al. Acta Pharm. Suec. (1974), 11(3), 304-308; Nyberg, K. et.al. Acta Chem. Scand. (1970), 24, 1590-1596; and Cohen, V. I. et.al. J. Pharm. Sciences (1992), 81, 326-329.

EXAMPLE I-1a

Preparation of (Furan-2-yl)hydroxyphenylacetic acid 1-azabicyclo[2.2.2]oct-3(R)-yl ester 3.24 g (0.014 mols) of (Furan-2-yl)-hydroxy-phenylacetic acid methyl ester were dissolved in 85 ml of toluene. To this solution were added 2.08 g (0.016 mols) of 3-(R)-hydroxy-1-azabicyclo[2.2.2]octane and 0.224 g (5.6 mmols) of HNa (60% dispersion in mineral oil). The mixture was refluxed with continuous removal of distillate and when necessary replacement with fresh toluene for 1.5 hours. The cooled mixture was extracted with 2N HCl acid, the aqueous layer washed with ethyl acetate, basified with K2CO3 and extracted with CHCl3. The organic layer was dried over Na2SO4 and evaporated. The oil obtained (3.47 g) crystallised after cooling at room temperature. This solid was suspended in hexane and filtered. The yield was 2.5 g (54%) of a mixture of diasteroisomers, mp: 140-142° C.;GC/MS [M]$^+$: 327; $^1$H-NMR (CDCl3): δ 1.20-1.70 (m, 4H), 1.90-2.10 (m, 1H), 2.45-2.80 (m, 5H), 3.10-3.30 (m, 1H), 4.8 (bs, OH), 4.90-5.0 (m, 1H), 6.20 (m, 1H), 6.35 (m, 1H), 7.30-7.50 (m, 4H), 7.60-7.70 (m, 2H).

After four crystallizations of 0.5 g of this mixture from boiling acetonitrile, 0.110 g of a pure diastereomer(1) were obtained. From the mother liquors of crystallization was obtained the other diastereomer (2). (*: configuration not assigned). Diastereomer 1 was hydrolysed to yield (+)-2-hydroxy-2-phenyl-2-furan-2-ylacetic acid as a pure enantiomer, $[\alpha]^{25}_D$=+5.6 (c=2, EtOH). Diastereomer 2 was hydrolysed to yield (−)-2-hydroxy-2-phenyl-2-furan-2-ylacetic acid as a pure enantiomer, $[\alpha]^{25}_D$=−5.7 (c=2, EtOH).

Diastereomer 1: 2(*)-(Furan-2-yl)hydroxyphenylacetic acid 1-azabicyclo[2.2.2]oct-3(R)-yl ester. $^1$H-NMR (CDCl3): δ 1.20-1.70 (m, 4H), 1.90 (m, 1H), 2.45-2.50 (m, 1H), 2.50-2.80 (m, 4H), 3.10-3.20 (m, 1H), 4.8 (bs, OH), 4.90-5.0 (m, 1H), 6.20 (m, 1H), 6.35 (m, 1H), 7.30-7.50 (m, 4H), 7.60-7.70 (m, 2H).

Diastereomer 2:2(*)-(Furan-2-yl)hydroxyphenylacetic acid 1-azabicyclo[2.2.2]oct-3(R)-yl ester. $^1$H-NMR (CDCl3): δ 1.20-1.70 (m, 4H), 2.10 (m, 1H), 2.50-2.80 (m, 5H), 3.20-3.30 (m, 1H), 4.8 (bs, OH), 4.90-5.0 (m, 1H), 6.20 (m, 1H), 6.35 (m, 1H), 7.30-7.50 (m, 4H), 7.60-7.70 (m, 2H).

EXAMPLE I-1b

Preparation of Furan-2-ylhydroxythien-2-ylacetic acid 1-azabicyclo[2.2.2]oct-3(R)-yl ester Prepared as in example I-1a. The yield was 3.06 g (64.3%) of a mixture of diastereoisomers, mp: 1721 C; GC/MS [M]$^+$: 333; $^1$H-NMR (DMSO-d6): δ 1.21-1.27 (m, 1H), 1.41-1.60 (m, 3H), 1.87 (m, 1H), 2.36-2.69 (m, 5H), 3.02-3.14 (m, 1H), 4.75-4.82 (m, 1H), 6.24-6.25 (m, 1H), 6.42-6.45 (m, 1H), 7.01-7.06 (m, 1H), 7.11-7.14 (m, 2H), 7.51-7.54 (m, 1H), 7.66-7.69 (m, 1H).

EXAMPLE I-1c

Preparation of 9-Methyl-9[H]-fluorene-9-carboxylic acid 1-azabicyclo[2.2.2]oct-3(R)-yl ester Prepared as in example I-1a. The yield was 3.34 g of an oil (80%). This product was solidified by formation of the oxalate salt (1:1), mp: 1861 C. MS [M free base+1]$^+$: 334. Oxalate salt, $^1$H-NMR (DMSO-d6): δ 1.43-1.55 (m, 2H), 1.68-1.78 (m, 1H), 1.75 (s, 3H), 2.02 (m, 1H), 2.70-2.90 (m, 1H), 2.92-3.15 (m, 4H), 3.50-3.57 (m, 1H), 4.88 (m, 1H), 7.35-7.47 (m, 4H), 7.62-7.70 (m, 2H), 7.89-7.91 (m, 2H).

EXAMPLE I-1d

Preparation of 9-Methyl-9[H]-xanthene-9-carboxylic acid 1-azabicyclo[2.2.2]oct-3(R)-yl ester Prepared as in example I-1a. The yield was 1.91 g of an oil (53%). This product was solidified by formation of the oxalate salt (1:1), mp: 1521 C. MS [M free base+1]$^+$: 350. Oxalate salt, $^1$H-NMR (DMSO-d6): δ 1.20-1.30 (m, 1H), 1.40-1.52 (m, 1H), 1.64-1.81 (m, 2H), 1.90 (s, 3H), 2.0 (m, 1H), 2.53-2.66 (m, 1H), 2.71-2.76 (m, 1H), 2.97-3.10 (m, 3H), 3.44-3.52 (m, 1H), 4.90-4.92 (m, 1H), 7.12-7.18 (m, 4H), 7.32-7.38 (m, 2H), 7.43-7.48 (m, 2H), 8.0-9.8 (bs, 1H, H$^+$).

EXAMPLE I-1e

Preparation of 9-Methyl-9[H]-fluorene-9-carboxylic acid methyl ester

Lithium diisopropylamide (26.7 ml of a 2M solution in heptane/tetrahydrofurane/ethylbenzene, 0.053 mol) was added to a stirred solution of 9[H]-fluorene-9-carboxylic acid (5 g, 0.0237 mol) in THF (70 ml) at between 0 and 51 C in N$_2$ atmosphere. The mixture was warmed to room temperature and refluxed 1.5 hours. The reaction mixture was cooled to room temperature and a solution of CH3I (1.85 ml, 0.03 mol) in THF (1.85 ml) was added. The mixture was stirred overnight at room temperature and evaporated. To the residue in MeOH (70 ml) was added concentrated sulfuric acid (3.9 ml) in MeOH (25 ml), the mixture was refluxed for 2 hours and evaporated. The residue was partitioned between chloroform and saturated K2CO3 solution. The aqueous layer was extracted again with chloroform and the organic layers were combined, washed with water, dried over sodium sulphate and evaporated to dryness to obtain 5.73 g of a brown oil. This product was purified by column chromatography (silica gel, hexane/ethyl acetate 95:5) to yield 4.43 g (78.5%) of a pure product, structure confirmed by $^1$H-NMR.

$^1$H-NMR (CDCl3): δ 1.80 (s, 3H), 3.60 (s, 3H), 7.50-7.65 (m, 4H), 7.75 (m, 2H), 8.0 (m, 2H).

EXAMPLE I-1f

Preparation of 9-Methyl-9[H]-xanthene-9-carboxylic acid methyl ester

Prepared as in example I-1e. The yield was 2.65 g (47.2%). $^1$H-NMR (CDCl3): δ 1.90 (s, 3H), 3.6 (s, 3H), 7.05-7.35 (m, 8H).

EXAMPLE I-1g

Preparation of 9-Hydroxy-9[H]-xanthene-9-carboxylic acid methyl ester

Lithium diisopropylamide (20.3 ml of a 2M solution in heptane/tetrahydrofurane/ethylbenzene, 0.041 mol) was added to a stirred solution of 7 g (0.029 mol) of 9[H]-xantene-9-carboxylic acid methyl ester (prepared by a standard method) in THF (70 ml) at between 0 and 51 C in N$_2$ atmosphere. The mixture was stirred 1 h at this temperature and then was added by N2 pressure to a dry solution of oxygen in ether at 01 C. After 30 min, an equal volum of NaHSO3, 40% aqueous solution, was added, and the reaction mixture was warmed to room temperature and stirred for 30 min. The two layers were separated and the aqueous phase was extracted twice with ethyl acetate. The organic phases were combined, treated with NaHSO3 (40% aqueous solution), washed with water, dried over-sodium sulphate and evaporated to dryness to obtain 8.89 g of a brown solid.

This procedure was repeated with 5 g of starting material yielding 6.04 g of the same brown solid.

The products were combined and purified by column chromatography (silica gel, hexane/ethyl acetate 90:10) to yield 7.60 g (global Rt: 59.4%) of a pure product, structure confirmed by $^1$H-NMR.

$^1$H-NMR (DMSO-d6): δ 3.5 (s, 3H), 7.0 (s, 1H, OH), 7.2 (m, 4H), 7.4 (m, 2H), 7.55 (m, 2H).

Method - d -

EXAMPLE I-2a

Preparation of 10,11-Dihydro-5[H]-dibenzo[a,d] cycloheptane-5-carboxylic acid 1-azabicyclo[2.2.2]oct-3-(R)-yl ester 2.15 g of 10,11-Dihydro-5[H]-dibenzo[a,d]cycloheptane-5-carboxylic acid (9.0 mmol) were dissolved in 40 ml of CHCl3 (ethanol free). The solution was cooled at 0° C. and 0.86 ml of oxalyl chloride (9.9 mmols) and a drop of DMF were added. The mixture was stirred and allowed warm to room temperature. After an hour at this temperature the solvents were evaporated and the residue was dissolved in CHCl3 and evaporated again. This procedure was repeated two times. The obtained oil was dissolved in 20 ml of toluene and added to a solution of 1.26 g (9.9 mmol) of 3(R)-hydroxy-1-azabicyclo[2.2.2]octane in 40 ml of hot toluene. The reaction mixture was refluxed for 2 hours. After cooling the mixture was extracted with 2N HCl acid. The aqueous layer was basified with K2CO3 and extracted with CHCl3. The organic layer was dried over Na2SO4 and evaporated to dryness. The residue was purified by column chromatography (silica gel, CHCl3:MeOH:NH4OH, 95:5: 0.5). The yield was 1.5 g (48%); mp: 112-113° C.; CG/MS [M]$^+$: 347; $^1$H-NMR (CDCl3): δ 1.10-1.35 (m, 2H), 1.40-1.52 (m, 1H), 1.52-1.68 (m, 1H), 1.90 (m, 1H), 2.40-2.60 (m, 2H), 2.60-2.77 (m, 3H), 2.83-2.96 (m, 2H), 3.07-3.19 (m, 1H), 3.25-3.40 (m, 2H), 4.80 (m, 2H), 7.10-7.30 (m, 8H).

10,11-Dihydro-5[H]-dibenzo[a,d]cycloheptane-5-carboxylic acid was prepared as described in Kumazawa T. et al., J. Med. Chem., (1994), 37, 804-810.

EXAMPLE I-2b

Preparation of 5[H]-Dibenzo[a,d]cycloheptene-5-carboxylic acid 1-azabicyclo[2.2.2]oct-3-(R)-yl ester Prepared as in example I-2a. The yield was 3.12 g (71%); mp 1291 C; MS [M+1]$^+$: 346; $^1$H-NMR (DMSO-d6): δ 0.90-1.10 (m, 2H), 1.30-1.50 (m, 2H), 1.58 (m, 1H), 2.21-2.26 (m, 2H), 2.47-2.50 (m, 3H), 2.86-2.94 (m, 1H), 4.48-4.51 (m, 1H), 5.33 (s, 1H), 7.0 (m, 2H), 7.29-7.43 (m, 6H), 7.49-7.51 (m, 1H).

5[H]-Dibenzo[a,d]cycloheptene-5-carboxylic acid was prepared as described in M. A. Davis et al; J. Med. Chem., (1964), Vol 7, 88-94.

EXAMPLE I-2c

Preparation of 9,10-Dihydroanthracene-9-carboxylic acid 1-azabicyclo[2.2.2]oct-3-(R)-yl ester Prepared as in example I-2a. The yield was 0.77 g (62.6%); mp 1391 C; MS [M+1]$^+$: 334; $^1$H-NMR (DMSO-d6): δ 1.1-1.2 (m, 1H), 1.25-1.40 (m, 2H), 1.40-1.55 (m, 1H), 1.73 (m, 1H), 2.20 (m, 1H), 2.35-2.65 (m, 4H), 2.90-2.98 (m, 1H), 3.93-4.14 (dd, 2H, J=1.8 Hz, J=4.3 Hz), 4.56 (m, 1H), 5.14 (s, 1H), 7.25-7.35 (m, 4H), 7.35-7.50 (m, 4H).

9,10-Dihydro-anthracene-9-carboxylic acid was prepared as described in E. L. May and E. Mossettig; J. Am. Chem. Soc., (1948), Vol 70, 1077-9.

Method - e -

EXAMPLE I-3

Preparation of 2,2-Diphenylpropionic acid 1-azabicyclo-[2.2.2]oct-3(R)-yl ester 1.1 g (4.8 mmol) of 2,2-diphenylpropionic acid were dissolved in 20 ml of THF. To this solution were added 0.87 g (5.3 mmol) of 1,1=-carbonyldiimidazole and the mixture was refluxed for an hour. The reaction was monitored by TLC following the formation of the imidazolide. When the reaction was completed part of the solvent was evaporated and 0.67 g (5.3 mmol) of 3-(R)-hydroxy-1-azabicyclo[2.2.2] octane were added. The reaction mixture was refluxed for 16 h, cooled, diluted with ether and washed with water. The organic layer was extracted with HCl 2N, the acid solution basified with K2CO3 and extracted with CHCl3. The organic solution was dried over Na2SO4 and evaporated to dryness to yield 1.21 g (75.2%) of an oil that was identified as the title ester.

0.64 g (1.9 mmol) of 2,2-Diphenylpropionic acid 1-azabicyclo [2.2.2]oct-3(R)-yl ester were dissolved in 6 ml of ketone and 0.085 g (0.95 mmol) of oxalic acid were added. After slow addition of ether a white solid was formed. The yield was 0.33 g (45.6%) of oxalate of 2,2-Diphenylpropionic acid 1-azabicyclo[2.2.2]oct-3(R)-yl ester; mp: 1461 C; MS [M free base+1]$^+$: 336.

Oxalate salt, $^1$H-NMR (CDCl3): δ 1.40-1.64 (m, 2H), 1.90 (s, 3H), 1.80-2.0 (m, 2H), 2.31 (m, 1H), 2.73-2.85 (m, 1H), 3.0-3.10 (m, 1H), 3.10-3.32 (m, 3H), 3.53-3.70 (m, 1H), 5.13 (m, 1H), 7.14-7.40 (m, 10H), 9.25 (broad band, 2H, H$^+$).

Method - f -

EXAMPLE I-4a

Preparation of 2-Hydroxy-2,2-dithien-2-ylacetic acid 1-azabicyclo[2.2.2]oct-4-yl ester A solution of 2-thienylmagnesium bromide was prepared from 220 mg (9 mmols) of Magnesium and 0.86 ml (9 mmols) of 2-bromothiophene in 15 ml of THF. This solution was added to 1.95 g (7 mmols) of oxothien-2-yl-acetic acid 1-azabicyclo[2.2.2]oct-4-yl ester (intermediate I-4b) dissolved in 20 ml of THF. The mixture was stirred at room temperature for 1 hour, refluxed for 1 hour, cooled, treated with a saturated solution of ammonium chloride and extracted with ether. After removal of the solvent the solid obtained was recrystallised from acetonitrile to yield 1.45 g, of a white solid (56%). $^1$H-NMR (DMSO-d6): δ 1.80-2.0 (m, 6H), 2.80-3.0 (m, 6H), 7.0 (m, 2H), 7.13 (m, 2H), 7.18 (s, 1H), 7.51 (m, 2H); MS [M+1]: 350; mp 174° C.

EXAMPLE I-4b

Preparation of oxothien-2-yl-acetic acid 1-azabicyclo[2.2.2]oct-4-yl ester

Oxalyl chloride (1.5 ml, 0.017 mol) was added to a solution of oxothien-2-yl-acetic acid (2.24 g, 0.014 mol) and dimethylformamide (one drop) in 30 ml of chloroform (etanol free) at 01 C. The mixture was stirred and allowed to warm at room temperature. After one hour the solvent was evaporated. The residue was dissolved in chloroform and evaporated again. This procedure was repeated two times. The product obtained was disolved in CHCl3 (30 ml) and added to a suspension of 1.1 g (0.009 mols) of 4-hydroxy-1-azabicyclo[2.2.2]octane, 1.8 ml of triethylamine (0.013 mols), 0.6 g (0.9 mmols) of N-(methylpolystyrene)-4-(methylamino) pyridine at 70° C. The mixture was refluxed for 1 hour, cooled, filtered and washed with water. The title product was extracted with a solution of diluted HCl, washed with CHCl3, basified with K2CO3 and extracted again with CHCl3. After removal of the solvent 1.47 g (45%) of a solid was obtained. $^1$H-NMR (dmso): δ 2.0 (m, 6H), 2.9 (m, 6H), 7.35 (m, 1H), 8.05 (m, 1H), 8.3 (m, 1H).

EXAMPLE I-4c

Preparation of (Furan-2-yl)hydroxyphenylacetic acid 1-azabicyclo[2.2.2]oct-3(R)-yl ester Phenylmagnesium bromide, 0.0057 mol (5.7 ml of a solution 1M in THF), was added to a solution of 1.3 g (0.0052 mol) of oxofuran-2-ylacetic acid 1-azabicyclo [2.2.2]oct-3(R)-yl ester (intermediate I-4e-) dissolved in 15 ml of THF, at −701 C in N2 atmosphere. The mixture was stirred at this temperature for 10 minuts, and then warmed to room temperature. After 1 hour, the reaction mixture was treated with a saturated solution of ammonium chloride and extracted three times with ethyl acetate The organic phases were combined, washed with water and dried over Na2SO4. After removal of the solvent, the solid obtained was treated with ether and filtered to yield 0.67 g (40%) of a product whose structure was confirmed by $^1$H-NMR. This compound was also prepared as is described in Example I-1a (Method c). The diastereomers were separated by crystallization from acetonitrile and distinguished by $^1$H-NMR.

EXAMPLE I-4d

Preparation of 2-Hydroxy-2,2-difur-2-yl-acetic acid 1-azabicyclo[2.2.2]oct-3(R)-yl ester The title compound was synthesised as in example I-4c from intermediate I-4e- and 2-furanyl lithium which was prepared with furane and butyl lithium following a standard method. The yield was 380 mg (8%). $^1$H-NMR (CDCl3): δ 1.2-1.4 (m, 1H), 1.4-1.8 (m, 3H), 2.0 (m, 1H), 2.6-2.85 (m, 5H), 3.2 (m, 1H), 5.0 (m, 1H), 6.4 (m, 3H), 7.3 (m, 1H), 7.5 (m, 2H). MS [M+1]$^+$: 318.

EXAMPLE I-4e

Preparation of oxofuran-2-yl-acetic acid 1-azabicyclo[2.2.2]oct-3(R)-yl ester

Oxalyl chloride (9.75 ml, 0.112 mol) was added to a solution of oxofuran-2-ylacetic acid (10 g, 0.071 mol) and dimethylformamide (one drop) in 150 ml of chloroform (etanol free) at 01 C. The mixture was stirred and allowed to warm at room temperature. After five hours the solvent was evaporated. The residue was dissolved in chloroform and evaporated again. This procedure was repeated two times. The product obtained was disolved in CHCl3 (150 ml) and a solution of 3(R)-quinuclidinol (10.90 g, 0.086 mol) in CHCl3 (150 ml) was added to this at 01 C. The mixture was stirred and allowed to warm at room temperature. After 15 h at r.t., the mixture was washed with 10% aqueous potassium carbonate, then with water, dried over Na2SO4 and evaporated to give 9.34 g (52.5%) of the title compound as a dark oil. Structure confirmed by NMR.

$^1$H-NMR (CDCl3): δ 1.40-1.60 (m, 1H), 1.60-1.80 (m, 2H), 1.80-2.05 (m, 1H), 2.20 (m, 1H), 2.70-3.10 (m, 5H), 3.30-3.45 (m, 1H), 5.10 (m, 1H), 6.7 (m, 1H), 7.7 (m, 1H), 7.8 (m, 1H).

EXAMPLE I-4f

Preparation of 2-Hydroxy-2-phenyl-2-thien-2-ylacetic acid 1-azabicyclo[2.2.2]oct-3(R)-yl ester The title compound was prepared as described in example I-4c from intermediate I-4g. The yield was 3 g (33%) as a mixture of diastereomers. After five crystallizations of 1.5 g of this mixture from boiling isopropanol, 0.200 g of a pure diastereomer(1) were obtained. The mother liquors from first crystallization were enriched with the other diastereomer (2). Diastereomer 1 was hidrolysed to yield (+)-2-Hydroxy-2-phenyl-2-thien-2-ylacetic acid as a pure enantiomer, [α]$^{25}_D$=+25.4 (c=2, EtOH). This value was assigned to the R configuration provided that in literature (A. I. Meyers et.al. J. Org. Chem. (1980), 45(14), 2913) the 2(S) enantiomer has been described with [α]$^{25}_D$=−20 (c=2, EtOH).

Diastereomer 1: 2(R)-2-Hydroxy-2-phenyl-2-thien-2-ylacetic acid 1-aza bicyclo[2.2.2]oct-3(R)-yl ester. $^1$H-NMR (DMSO-d6): δ 1.1-1.25 (m, 1H), 1.3-1.6 (m, 3H), 1.83 (m, 1H), 2.4-2.7 (m, 5H), 3.1 (m, 1H), 4.8 (m, 1H), 7.0 (m, 2H), 7.05 (m, 1H), 7.3-7.4 (m, 3H), 7.4-7.45 (m, 2H), 7.5 (m, 1H).

Diastereomer 2: 2(S)-2-Hydroxy-2-phenyl-2-thien-2-ylacetic acid 1-aza bicyclo[2.2.2]oct-3(R)-yl ester. $^1$H-NMR (DMSO-d6): δ 1.1-1.25 (m, 1H), 1.4-1.6 (m, 3H), 1.9 (m, 1H), 2.3-2.7 (m, 5H), 3.05 (m, 1H), 4.8 (m, 1H), 7.0 (m, 2H), 7.05 (m, 1H), 7.3-7.4 (m, 3H), 7.4-7.45 (m, 2H), 7.5 (m, 1H).

EXAMPLE I-4g

Preparation of oxothien-2-yl-acetic acid 1-azabicyclo[2.2.2]oct-3(R)-yl ester

Oxalyl chloride (1.34 ml, 0.0154 mol) was added to a solution of oxothien-2-yl-acetic acid (2 g, 0.0128 mol) and dimethylformamide (one drop) in 30 ml of chloroform (etanol free) at 01 C. The mixture was stirred and allowed to warm at room temperature. After one hour the solvent was evaporated. The residue was dissolved in chloroform and evaporated again. This procedure was repeated two times. The product obtained was disolved in CHCl3 (30 ml) and a solution of 3(R)-quinuclidinol (1.95 g, 0.0154 mol) in CHCl3 (30 ml) was added to this at 01 C. The mixture was stirred and allowed to warm at room temperature. After 1.5 h at r.t., the mixture was washed with 10% aqueous potassium carbonate, then with water, dried over Na2SO4 and evaporated to give 3.14 g (92.6%) of the title compound as a yellow oil. $^1$H-NMR (CDCl3): δ 1.40-1.50 (m, 1H), 1.50-1.70 (m, 1H), 1.70-1.80 (m, 1H), 1.90-2.0 (m, 1H), 2.15 (m, 1H), 2.70-3.05 (m, 5H), 3.30-3.40 (m, 1H), 5.05 (m, 1H), 7.20 (m, 1H), 7.85 (m, 1H), 8.10 (m, 1H).

Other carboxylic acids of Formula B—C(O)OH, whose preparation (or the syntheses of their derivatives methyl ester, chloride or imidazolide) have not been described in methods c, d, e or in the Examples I-1e, I-1f and I-1g, and that are not commercially available, could be prepared as is described in the following references:

FR 2012964
M. A. Davis et al; J. Med. Chem. (1963), 6, 513-516.
T. Kumazawa et al; J. Med. Chem, (1994), 37(6), 804-810.
M. A. Davis et al; J. Med. Chem., (1964), Vol (7), 88-94.
Sestanj, K; Can. J. Chem., (1971), 49, 664-665.
Burtner, R.; J. Am. Chem. Soc., (1943), 65, 1582-1585
Heacock R. A. et al.; Ann. Appl. Biol., (1958), 46(3), 352-365.
Rigaudy J. et. al.; Bull. Soc. Chim. France, (1959), 638-43.
Ueda I. et al.; Bull. Chem. Soc. Jpn; (1975), 48 (8), 2306-2309.
E. L. May et. al.; J. Am. Chem. Soc., (1948), 70, 1077-9.

Also included within the scope of the present invention are pharmaceutical composition which comprise, as the active ingredient, at least one quinuclidine derivative of general formula (I) in association with a pharmaceutically acceptable carrier or diluent. Preferably the composition is made up in a form suitable for oral administration.

The pharmaceutically acceptable carrier or diluents which are mixed with the active compound or compounds, to form the composition of this invention are well-known per se and the actual excipients used depend inter alia on the intended method of administration of the composition.

Compositions of this invention are preferably adapted for oral administration. In this case, the composition for oral administration may take the form of tablets, film-coated tablets, liquid inhalant, powder inhalant and inhalation aerosol; all containing one or more compounds of the invention; such preparations may be made by methods well-known in the art.

The diluents which may be used in the preparations of the compositions include those liquid and solid diluents which are compatible with the active ingredient, together with colouring or flavouring agents, if desired. Tablets or film-coated tablets may conveniently contain between 500 and 1 mg, preferably from 5 to 300 mg of active ingredient. The inhalant compositions may contain between 1 Φg and 1,000 Φg, preferably from 10 to 80 Φg of active ingredient. In human therapy, the dose of the compound of general formula (I) depend on the desired effect and duration of treatment; adult doses are generally between 3 mg and 300 mg per day as tablets and 10 Φg and 800 Φg per day as inhalant composition.

Pharmacological Action

The following examples demonstrate the excellent pharmacological activities of the compounds of the present invention. The results on human muscarinic receptors binding and in the test on bronchospasm in guinea pig, were obtained as described below.

Human Muscarinic Receptor Studies.

The binding of [$^3$H]-NMS to human muscarinic receptors was performed according to Waelbroek et al (1990) (1). Assays were carried out at 25° C. Membrane preparations from stably transfected chinese hamster ovary-K1 cells (CHO) expressing the genes for the human muscarinic receptors Hm3 were used.

For determination of IC$_{50}$, membrane preparations were suspended in DPBS to a final concentration of 89 μg/ml for the Hm3 subtype. The membrane suspension was incubated with the tritiated compound for 60 min. After incubation the membrane fraction was separated by filtration and the bound radioactivity determined. Non specific binding was determined by addition of $10^{-4}$ M atropine. At least six concentrations were assayed in duplicate to generate individual displacement curves.

| COMPOUNDS No | BINDING TO RECEPTOR M$_3$ (IC$_{50}$ nM) |
|---|---|
| ATROPINE | 3.2 |
| IPRATROPIUM | 3.0 |
| 1 | 31 |
| 2 | 15 |
| 7 | 22 |
| 8 | 4.8 |
| 17 | 14 |
| 18 | 6.6 |
| 20 | 6.8 |
| 35 | 13 |
| 36 | 2.7 |
| 39 | 3.8 |
| 44 | 4.4 |
| 53 | 5.6 |
| 71 | 8.2 |
| 74 | 16 |
| 77 | 3.1 |
| 78 | 5 |
| 84 | 9.9 |
| 89 | 5.4 |
| 99 | 31 |
| 100 | 14 |
| 101 | 7.6 |
| 109 | 31 |
| 114 | 14 |
| 116 | 23 |
| 126 | 13 |
| 127 | 16 |
| 128 | 8.8 |
| 129 | 6.3 |
| 136 | 11 |
| 137 | 6.9 |
| 138 | 19 |
| 146 | 13 |

(1) M. Waelbroek M. Tastenoy, J. Camus, J Christophe. Binding of selective antagonists to four muscarinic receptors (M1 to M4) in rat forebrain Mol. Pharmacol. (1990) 38: 267-273.

Our results show that the compounds of the present invention have affinities for the M$_3$ receptors which are very similar to the reference compounds.

The compounds of the invention preferably have high affinities for muscarinic M$_3$ receptors (HM3), preferably human muscarinic receptors. Affinity levels can typically be measured by in vitro assays, for example, as described above.

Preferred compounds of the invention have an IC$_{50}$ (nM) value for M$_3$ receptors of less than 35, preferably less than 25, 20 or 15, more preferably less than 10, 8 or 5.

Test on Bronchospasm in Guinea Pig

The studies were performed according to Konzett and Rössler (2). Aqueous solutions of the agents to be tested were nebulized and inhaled by anaesthetized ventilated male guinea pigs (Dunkin-Hartley). The bronchial response to intravenous acetylcholine challenge was determined before and after drug administration and the percent change in pulmonary resistance at several time-points.

2. Konzett H., Rössler F. Versuchsanordnung zu Untersuchungen ander bronchialmuskulatur. Arch. Exp. Path. Pharmacol. 195: 71-74 (1940)

The compounds of the present invention inhibited the bronchospasm response to acetylcholine with high potency and a long duration of action.

From the above described results one of ordinary skill in the art can readily understand that the compounds of the present invention have excellent antimuscarinic activity ($M_3$) and thus are useful for the treatment of diseases in which the muscarinic $M_3$ receptor is implicated, including respiratory diseases such as chronic obstructive pulmonary disease, chronic bronchitis, asthma and rhinitis, urinary diseases such as urinary incontinence and pollakinuria in neuripenia pollakinuria, neurogenic bladder, nocturnal enuresis, unstable bladder, cystospasm and chronic cystitis and gastrointestinal diseases such as irritable bowel syndrome, spastic colitis and diverticulitis.

The present invention further provides a compound of formula (I) or a pharmaceutically acceptable composition comprising a compound of formula (I) for use in a method of treatment of the human or animal body by therapy, in particular for the treatment of respiratory, urinary or gastrointestinal disease.

The present invention further provides the use of a compound of formula (I) or a pharmaceutically acceptable composition comprising a compound of formula (I) for the manufacture of a medicament for the treatment of respiratory, urinary or gastrointestinal disease.

Further, the compounds of formula (I) and pharmaceutical compositions comprising a compound of formula (I) can be used in a method of treating respiratory, urinary or gastrointestinal disease, which method comprises administering to a human or animal patient in need of such treatment an effective amount of a compound of formula (I) or a pharmaceutical composition comprising a compound of formula (I).

The present invention will be further illustrated by the following examples. The examples are given by way of illustration only and are not to be construed as limiting.

EXAMPLE 1

3(R)-Diphenylacetoxy-1-(3-phenoxypropyl)-1-azoniabicyclo[2.2.2]octane; bromide

The title compound was synthesised according to methods d and a. The yield of final step was 500 mg, 81%. $^1$H-NMR (CDCl$_3$): δ 1.72-2.18 (m, 6H), 2.35 (m, 1H), 3.0 (m, 1H), 3.23 (m, 1H), 3.59-3.88 (m, 5H), 4.0 (m, 2H), 4.30 (m, 1H), 5.1 (s, 1H), 5.25 (m, 1H), 6.8-6.9 (m, 2H), 6.9-7.0 (m, 1H), 7.2-7.4 (m, 12H); MS [M-Br]$^+$: 456; mp 129° C.

EXAMPLE 2

3(R)-(2-Hydroxy-2,2-diphenylacetoxy)-1-(3-phenoxypropyl)-1-azoniabicyclo[2.2.2]octane; bromide The title compound was synthesised according to methods c and a. The yield of final step was 280 mg, 42%. $^1$H-NMR (DMSO-d6): δ 1.5-1.7 (m, 2H), 1.9-2.1 (m, 4H), 2.3 (m, 1H), 3.1 (m, 1H), 3.2-3.5 (m, 6H), 3.9-4.1 (m, 3H), 5.25 (m, 1H), 6.8 (bs, OH), 6.95 (m, 3H), 7.2-7.5 (m, 12H); MS [M-Br]$^+$: 472; mp 199° C.

EXAMPLE 3

3(R)-[2,2-Bis(4-fluorophenyl)-2-hydroxyacetoxy]-1-(3-phenoxypropyl)-1-azoniabicyclo[2.2.2]octane; bromide The title compound was synthesised according to methods c and a. The yield of final step was 400 mg, 85%. $^1$H-NMR (DMSO-d6): δ 1.5-1.65 (m, 1H), 1.7-1.8 (m, 1H), 1.85-2.0 (m, 2H), 2.05-2.2 (m, 2H), 2.3 (m, 1H), 3.1-3.2 (m, 1H), 3.3-3.5 (m, 6H), 3.95 (m, 1H), 4.05 (m, 2H), 5.25 (m, 1H), 6.9-7.0 (m, 4H), 7.1-7.5 (m, 10H); MS [M-Br]$^+$: 508; mp 253° C.

EXAMPLE 4

3(R)-[2,2-Bis(4-fluorophenyl)-2-hydroxyacetoxy]-1-phenethyl-1-azoniabicyclo[2.2.2]octane; bromide The title compound was synthesised according to methods c and a. The yield of final step was 300 mg, 67%. $^1$H-NMR (DMSO-d6): δ 1.5-1.65 (m, 1H), 1.7-1.85 (m, 1H), 1.85-2.1 (m, 2H), 2.3 (m, 1H), 2.9-3.1 (m, 2H), 3.15-3.25 (m, 1H), 3.3-3.6 (m, 6H), 3.95-4.05 (m, 1H), 5.25 (m, 1H), 6.95 (s, OH), 7.1-7.5 (m, 13H); MS [M-Br]$^+$: 478; mp 182° C.

EXAMPLE 5

3(R)-(2-Hydroxy-2,2-di-p-tolylacetoxy)-1-(3-phenoxypropyl)-1-azoniabicyclo[2.2.2]octane; bromide The title compound was synthesised according to methods c and a. The yield of final step was 500 mg, 54%. $^1$H-NMR (DMSO-d6): δ 1.55-1.8 (m, 2H), 1.85-2.0 (m, 2H), 2.05-1.15 (m, 2H), 2.3 (s, 7H), 3.05-3.15 (m, 1H), 3.25-3.5 (m, 6H), 3.95 (m, 1H), 4.05 (t, 2H), 5.2 (m, 1H), 6.8 (s, OH), 6.95 (m, 3H), 7.1-7.2 (m, 4H), 7.2-7.35 (m, 6H); MS [M-Br]$^+$:500; mp 183° C.

EXAMPLE 6

3(R)-(2-Hydroxy-2,2-di-p-tolylacetoxy)-1-phenethyl-1-azoniabicyclo[2.2.2]octane; bromide The title compound was synthesised according to methods c and a. The yield of final step was 650 mg, 74%. $^1$H-NMR (DMSO-d6): δ 1.55-1.8 (m, 2H), 1.85-2.05 (m, 2H), 2.25 (s, 7H), 2.9-3.05 (m, 2H), 3.1-3.25 (m, 1H), 3.3-3.55 (m, 6H), 3.95 (m, 1H), 5.25 (m, 1H), 6.8 (s, OH), 7.1-7.2 (m, 4H), 7.2-7.35 (m, 9H); MS [M-Br]$^+$:470; mp 144° C.

EXAMPLE 7

3(R)-(2,2-Diphenylpropionyloxy)-1-(3-phenoxypropyl)-1-azoniabicyclo[2.2.2]octane; bromide The title compound was synthesised according to methods e and a. The yield of final step was 250 mg, 61%. $^1$H-NMR (CDCl$_3$): δ 1.47-1.60 (m, 1H), 1.8-2.0 (m, 1H), 2.0 (s, 3H), 2.0-2.15 (m, 4H), 2.39 (s, 1H), 2.6 (m, 1H), 2.92 (d, 1H), 3.6 (m, 1H), 3.7-3.9 (m, 4H), 4.0 (m, 2H), 4.3 (m, 1H), 5.25 (m, 1H), 6.85 (m, 2H), 7.0 (m, 1H), 7.3 (m, 12H); MS [M-Br]$^+$: 470; mp 186° C.

EXAMPLE 8

3(R)-(2-Hydroxy-2-phenyl-2-thien-2-ylacetoxy)-1-(3-phenoxypropyl)-1-azoniabicyclo[2.2.2]octane; bromide The title compound was synthesised as a mixture of diastereomers according to methods c and a. The yield of final step was 520 mg, 62%. $^1$H-NMR (DMSO-d6): δ 1.5-1.95 (m, 4H), 2.1 (m, 2H), 2.3 (m, 1H), 3.1 (m, 1H), 3.3-3.5 (m, 6H), 3.9 (m, 1H), 4.05 (t, 2H), 5.2 (m, 1H), 7.0 (m, 4H), 7.15 (m, 2H), 7.35 (m, 5H), 7.5 (m, 3H); MS [M-Br]$^+$: 478; mp 220° C.

EXAMPLE 9

3(R)-[2(R)-(2-Hydroxy-2-phenyl-2-thien-2-ylacetoxy)]-1-(3-phenoxypropyl)-1-azoniabicyclo[2.2.2]octane; trifluoroacetate The title compound was synthesised according to methods f and b from intermediate I-4f, diastereomer 1. The yield of final step was 10 mg, 23%. $^1$H-NMR (DMSO-d6): δ 1.5-1.6 (m, 1H), 1.65-1.75 (m, 1H), 1.8-2.0 (m, 2H), 2.05-2.1 (m, 2H), 2.3 (m, 1H), 3.05-3.2 (m, 1H), 3.25-3.55 (m, 6H), 3.85-3.95 (m, 1H), 4.0 (t, 2H), 5.2 (m, 1H), 6.95 (m, 3H), 7.03 (m, 1H), 7.15 (dd, 1H), 7.2 (s, OH), 7.3-7.5 (m, 5H), 7.45-7.55 (m, 3H); MS [M-CF3COO]$^+$: 478.

EXAMPLE 10

3(R)-[2(S)-(2-Hydroxy-2-phenyl-2-thien-2-ylacetoxy)]-1-(3-phenoxy propyl)-1-azoniabicyclo[2.2.2]octane; trifluoroacetate The title compound was synthesised according to methods f and b from intermediate I-4f, diastereomer 2. The yield of final step was 3 mg, 11%. $^1$H-NMR (DMSO-d6): δ 1.6-1.75 (m, 2H), 1.8-2.0 (m, 4H), 2.25 (m, 1H), 2.8 (t, 2H), 2.95-3.1 (m, 1H), 3.15-3.5 (m, 6H), 3.8-3.95 (m, 1H), 5.2 (m, 1H), 6.92 (m, 1H), 6.96-7.03 (m, 2H), 7.1 (dd, 1H), 7.18 (s, OH), 7.3-7.4 (m, 4H), 7.43-7.5 (m, 2H), 7.51 (dd, 1H); MS [M-CF3COO]$^+$: 478.

EXAMPLE 11

3(R)-[2(R)-(2-Hydroxy-2-phenyl-2-thien-2-ylacetoxy)]-1-(3-phenylpropyl)-1-azoniabicyclo[2.2.2]octane; trifluoroacetate The title compound was synthesised according to methods f and b from intermediate I-4f, diastereomer 1. The yield of final step was 9 mg, 22%. $^1$H-NMR (DMSO-d6): δ 1.45-1.55 (m, 1H), 1.65-1.75 (m, 1H), 1.85-2.05 (m, 2H), 2.3 (m, 1H), 2.9-3.1 (m, 2H), 3.1-3.25 (m, 1H), 3.25-3.55 (m, 6H), 3.9-4.0 (m, 1H), 5.25 (m, 1H), 7.05 (m, 1H), 7.15 (m, 1H), 7.2 (m, 1H), 7.25-7.4 (m, 8H), 7.45 (m, 2H, 7.55 (m, 1H); MS [M-CF3COO]$^+$: 448.

EXAMPLE 12

3(R)-[2(R)-(2-Hydroxy-2-phenyl-2-thien-2-ylacetoxy)]-1-(3-phenylpropyl)-1-azoniabicyclo[2.2.2]octane; trifluoroacetate The title compound was synthesised according to methods f and b from intermediate I-4f, diastereomer 1. The yield of final step was 11 mg, 26%. $^1$H-NMR (DMSO-d6): δ 1.45-1.55 (m, 1H), 1.6-1.75 (m, 1H), 1.8-2.0 (m, 4H), 2.25 (m, 1H), 2.55 (t, 2H), 3.0-3.1 (m, 1H), 3.15-3.55 (m, 6H), 3.8-3.9 (m, 1H), 5.2 (m, 1H), 7.0 (m, 1H), 7.1 (m, 1H), 7.15-7.4 (m, 9H), 7.45 (m, 2H), 7.5 (m, 1H); MS [M-CF3COO]$^+$: 462.

EXAMPLE 13

3(R)-[2(R)-(2-Hydroxy-2-phenyl-2-thien-2-ylacetoxy)]-1-(2-thien-2-ylethyl)-1-azoniabicyclo[2.2.2]octane; trifluoroacetate The title compound was synthesised according to methods f and b from intermediate I-4f, diastereomer 1. The yield of final step was 10 mg, 24%. $^1$H-NMR (DMSO-d6): δ 1.45-1.55 (m, 1H), 1.65-1.75 (m, 1H), 1.8-2.0 (m, 2H), 2.3 (m, 1H), 3.1-3.6 (m, 9H), 3.9-4.0 (m, 1H), 5.25 (m, 1H), 7.0 (m, 3H), 7.15 (dd, 1H), 7.2 (s, OH), 7.3-7.4 (m, 3H), 7.45-7.55 (m, 4H); MS [M-CF3COO]$^+$:454.

EXAMPLE 14

3(R)-[2(R)-(2-Hydroxy-2-phenyl-2-thien-2-ylacetoxy)]-1-(3-thien-2-ylpropyl)-1-azoniabicyclo[2.2.2]octane; trifluoroacetate The title compound was synthesised according to methods f and b from intermediate I-4f, diastereomer 1. The yield of final step was 8 mg, 19%. $^1$H-NMR (DMSO-d6): δ 1.45-1.6 (m, 1H), 1.65-1.75 (m, 1H), 1.8-2.05 (m, 4H), 2.25 (m, 1H), 2.8 (t, 2H), 3.0-3.15 (m, 1H), 3.2-3.5 (m, 6H), 3.8-3.95 (m, 1H), 5.2 (m, 1H), 6.92 (m, 1H), 6.96-7.03 (m,2H), 7.13 (dd, 1H), 7.2 (s, OH), 7.3-7.4 (m, 4H), 7.45-7.5 (m, 2H), 7.52 (dd, 1H); MS [M-CF3COO]$^+$: 468.

EXAMPLE 15

3(R)-[2(S)-(2-Hydroxy-2-phenyl-2-thien-2-ylacetoxy)]-1-(3-thien-2-ylpropyl)-1-azoniabicyclo[2.2.2]octane; trifluoroacetate The title compound was synthesised according to methods f and b from intermediate I-4f, diastereomer 2. The yield of final step was 7 mg, 26%. $^1$H-NMR (DMSO-d6): δ 1.6-1.75 (m, 2H), 1.8-2.0 (m, 4H), 2.25 (m, 1H), 2.8 (t, 2H), 2.95-3.1 (m, 1H), 3.15-3.5 (m, 6H), 3.8-3.95 (m, 1H), 5.2 (m, 1H), 6.92 (m, 1H), 6.96-7.03 (m, 2H), 7.1 (dd, 1H), 7.18 (s, OH), 7.3-7.4 (m, 4H), 7.43-7.5 (m, 2H), 7.51 (dd, 1H); MS [M-CF3COO]$^+$: 468.

EXAMPLE 16

3(R)-[2(R)-(2-Hydroxy-2-phenyl-2-thien-2-ylacetoxy)]-1-(2-phenoxyethyl)-1-azoniabicyclo[2.2.2]octane; trifluoroacetate The title compound was synthesised according to methods f and b from intermediate I-4f, diastereomer 1. The yield of final step was 11 mg, 26%. $^1$H-NMR (DMSO-d6): δ 1.5-1.6 (m, 1H), 1.65-1.75 (m, 1H), 1.8-2.0 (m, 2H), 2.25 (m, 1H), 3.15-3.6 (m, 5H), 3.7 (m, 2H), 4.0 (m, 2H), 4.4 (m, 2H), 5.25 (m, 1H), 6.95-7.03 (m, 4H), 7.12 (dd, 1H), 7.2 (s, OH), 7.3-7.4 (m, 5H), 7.4-7.5 (m, 3H); MS [M-CF3COO]$^+$: 464.

EXAMPLE 17

3(R)-(2-Furan-2-yl-2-hydroxy-2-phenylacetoxy)-1-(3-phenylallyl)-1-azoniabicyclo[2.2.2.2]octane; bromide The title compound was synthesised as a mixture of diastereomers according to methods c and a. The yield of final step was 240 mg, 77%. $^1$H-NMR (DMSO-d6): δ 1.55-2.0 (m, 4H), 2.27 (m, 1H), 3.05-3.55 (m, 5H), 3.88-3.98 (m, 1H), 4.0-4.10 (m, 2H), 5.21 (m, 1H), 6.23-6.31 (double dd, 1H), 6.36-6.48 (m, 2H), 6.83-6.90 (dd, 1H), 6.95 (d, OH), 7.26-7.66 (m, 11H); MS [M-Br]$^+$: 444; mp 99° C.

EXAMPLE 18

3(R)-(2-Furan-2-yl-2-hydroxy-2-phenylacetoxy)-1-(2-phenoxyethyl)-1-azoniabicyclo[2.2.2]octane; bromide The title compound was synthesised as a mixture of diastereomers according to methods c and a. The yield of final step was 210 mg, 66%. $^1$H-NMR (DMSO-d6): δ 1.50-2.05 (m, 4H), 2.27 (m, 1H), 3.20 (m, 1H), 3.37-3.65 (m, 4H), 3.65-3.75 (m, 2H), 4.04 (m, 1H), 4.40 (m, 2H), 5.21 (m, 1H), 6.23-6.32 (double dd, 1H), 6.44 (m, 1H), 6.94-7.04 (m, 4H), 7.33-7.50 (m, 7H), 7.64 (m, 1H); MS [M-Br]$^+$: 448; mp 163° C.

EXAMPLE 19

3(R)-[2(*)-(2-Furan-2-yl-2-hydroxy-2-phenylacetoxy)]-1-(2-phenoxyethyl)-1-azoniabicyclo[2.2.2]octane; trifluoroacetate The title compound was synthesised according to methods c and b from intermediate I-1a, diastereomer 1. The yield of final step was 11 mg, 23%. $^1$H-NMR (DMSO-d6): δ 1.65-1.80 (m, 2H), 1.80-2.10 (m, 2H), 2.27 (m, 1H), 3.15-3.65 (m, 5H), 3.68 (m, 2H), 4.0 (m, 1H), 4.40 (t, 2H), 5.20 (m, 1H), 6.23 (d, 1H), 6.42 (m, 1H), 6.92-7.04 (m, 4H), 7.30-7.38 (m, 5H), 7.44-7.50 (m, 2H), 7.64 (m, 1H); MS [M-CF3COO]$^+$: 448.

EXAMPLE 20

3(R)-(2-Furan-2-yl-2-hydroxy-2-phenylacetoxy)-1-(3-phenoxypropyl)-1-azoniabicyclo[2.2.2]octane; bromide The title compound has been described in method -a-.

EXAMPLE 21

3(R)-[2(*)-(2-Furan-2-yl-2-hydroxy-2-phenylacetoxy)]-1-(3-phenoxypropyl)-1-azoniabicyclo[2.2.2]octane; bromide The title compound was synthesised according to methods c and a from intermediate I-1a, diastereomer 1. The yield of final step was 1.15 g 99%. $^1$H-NMR (DMSO-d6): δ 1.60-2.20 (m, 6H), 2.25 (m, 1H), 3.10 (m, 1H), 3.20-3.60 (m, 6H), 3.95 (m, 1H), 4.05 (m, 2H), 5.20 (m, 1H), 6.25 (dd, 1H), 6.45 (m, 1H), 6.95 (m, 4H), 7.30-7.50 (m, 7H), 7.70 (m, 1H); MS [M-Br]$^+$: 462; mp156° C.

EXAMPLE 22

3(R)-[2(*)-(2-Furan-2-yl-2-hydroxy-2-phenylacetoxy)]-1-(3-phenoxypropyl)-1-azoniabicyclo[2.2.2]octane; trifluoroacetate The title compound was synthesised-according to methods c and b from intermediate I-1a, diastereomer 2. The yield of final step was 10 mg, 20%. $^1$H-NMR (DMSO-d6): δ 1.50-2.20 (m, 6H), 2.25 (m, 1H), 3.10 (m, 1H), 3.20-3.60 (m, 6H), 3.95 (m, 1H), 4.05 (m, 2H), 5.20 (m, 1H), 6.35 (dd, 1H), 6.45 (m, 1H), 6.95 (m, 4H), 7.30-7.50 (m, 7H), 7.70 (m, 1H); MS [M-CF3COO]$^+$: 462.

EXAMPLE 23

3(R)-(2-Furan-2-yl-2-hydroxy-2-phenylacetoxy)-1-phenethyl-1-azoniabicyclo[2.2.2]octane; trifluoroacetate The title compound was synthesised as a mixture of diastereomers according to methods c and b. The yield of final step was 12 mg, 13%. $^1$H-NMR (DMSO-d6): δ 1.5 (m, 1H), 1.7 (m, 1H), 1.9-2.05 (m, 2H), 2.3 (m, 1H), 2.95 (m, 2H), 3.15 (m, 1H), 3.25-3.55 (m, 6H), 3.95 (m, 1H), 5.25 (m, 1H), 6.3 (d, 1H), 6.45 (m, 1H), 6.95 (d, 1H), 7.25-7.45 (m, 8H), 7.5 (m, 2H), 7.7 (m, 1H); MS [M-CF$_3$COO]$^+$: 432.

EXAMPLE 24

3(R)-[2(*)-(2-Furan-2-yl-2-hydroxy-2-phenylacetoxy)]-1-phenethyl-1-azoniabicyclo[2.2.2]octane; trifluoroacetate The title compound was synthesised according to methods c and b from intermediate I-1a, diastereomer 1. The yield of final step was 16 mg, 40%. $^1$H-NMR (DMSO-d6): δ 1.65-1.80 (m, 2H), 1.90-2.05 (m, 2H), 2.3 (m, 1H), 2.95 (m, 2H), 3.15 (m, 1H), 3.25-3.55 (m, 6H), 3.95 (m, 1H), 5.25 (m, 1H), 6.26 (dd, 1H), 6.46 (m, 1H), 6.95 (s, 1H, OH), 7.25-7.45 (m, 8H), 7.5 (m, 2H), 7.7 (m, 1H); MS [M-CF3COO]$^+$: 432.

EXAMPLE 25

3(R)-[2(*)-(2-Furan-2-yl-2-hydroxy-2-phenylacetoxy)]-1-phenethyl-1-azoniabicyclo[2.2.2]octane; trifluoroacetate The title compound was synthesised-according to methods c and b from intermediate I-1a, diastereomer 2. The yield of final step was 14 mg, 35%. $^1$H-NMR (DMSO-d6): δ 1.50-1.80 (m, 2H), 1.90-2.05 (m, 2H), 2.3 (m, 1H), 2.95 (m, 2H), 3.15 (m, 1H), 3.25-3.55 (m, 6H), 3.95 (m, 1H), 5.25 (m, 1H), 6.32 (dd, 1H), 6.46 (m, 1H), 6.95 (s, 1H, OH), 7.25-7.45 (m, 8H), 7.5 (m, 2H), 7.7 (m, 1H); MS [M-CF3COO]$^+$: 432.

EXAMPLE 26

3(R)-[2(*)-(2-Furan-2-yl-2-hydroxy-2-phenylacetoxy)]-1-(3-phenylpropyl)-1-azoniabicyclo[2.2.2]octane; trifluoroacetate The title compound was synthesised according to methods c and b from intermediate I-1a, diastereomer 1. The yield of final step-was 10 mg, 21%. $^1$H-NMR (DMSO-d6): δ 1.60-1.75 (m, 2H), 1.80-2.0 (m, 4H), 2.25 (m, 1H), 2.50-2.60 (m, 2H), 3.0 (m, 1H), 3.10-3.50 (m, 6H), 3.83 (m, 1H), 5.17 (m, 1H), 6.25 (d, 1H), 6.45 (m, 1H), 6.95 (s, 1H), 7.20-7.40 (m, 8H), 7.46-7.48 (m, 2H), 7.66 (m, 1H); MS [M-CF3COO]$^+$: 446.

EXAMPLE 27

3(R)-[2(*)-(2-Furan-2-yl-2-hydroxy-2-phenylacetoxy)]-1-(2-thien-2-ylethyl)-1-azoniabicyclo[2.2.2]octane; trifluoroacetate The title compound was synthesised according to methods c and b from intermediate I-1a, diastereomer 1. The yield of final step was 9 mg, 19%. $^1$H-NMR (DMSO-d6): δ 1.65-1.80 (m, 2H), 1.85-2.05 (m, 2H), 2.30 (m, 1H), 3.10-3.40 (m, 3H), 3.40-3.60 (m, 6H), 3.95 (m, 1H), 5.24 (m, 1H), 6.27 (d, 1H), 6.47 (m, 1H), 6.96 (s, 1H), 7.0-7.04 (m 2H), 7.36-7.48 (m, 4H), 7.49-7.54 (m, 2H), 7.70 (m, 1H).; MS [M-CF3COO]$^+$: 438.

EXAMPLE 28

3(R)-[2(*)-(2-Furan-2-yl-2-hydroxy-2-phenylacetoxy)]-1-(3-thien-2-ylpropyl)-1-azoniabicyclo[2.2.2]octane; trifluoroacetate The title compound was synthesised according to methods c and b from intermediate I-1a, diastereomer 1. The yield of final step was 9 mg, 19%. $^1$H-NMR (DMSO-d6): δ 1.60-1.75 (m, 2H), 1.80-2.05 (m, 4H), 2.26 (m, 1H), 2.81 (t, 2H), 3.02 (m, 1H), 3.10-3.45 (m, 6H), 3.85 (m, 1H), 5.18 (m, 1H), 6.25 (d, 1H), 6.45 (m, 1H), 6.90-7.0 (m, 3H), 7.32-7.42 (m, 4H), 7.45-7.51 (m, 2H), 7.66 (m, 1H); MS [M-CF3COO]$^+$: 452.

EXAMPLE 29

3(R)-(2-Furan-2-yl-2-hydroxy-2-thien-2-ylacetoxy)-1-phenethyl-1-azoniabicyclo[2.2.2]octane; trifluoroacetate The title compound was synthesised as a mixture of diastereomers according to methods c and b. The yield of final step was 18 mg, 20%. $^1$H-NMR (DMSO-d6): δ 1.65-2.05 (m, 4H), 2.3 (m, 1H), 3.0 (m, 2H), 3.15-3.6 (m, 7H), 3.95 (m, 1H), 5.25 (m, 1H), 6.35 (dd, 1H), 6.45 (m, 1H), 7.05 (m, 1H), 7.2 (dd, 1H), 7.25-7.5 (m, 6H), 7.55 (m, 1H), 7.65 (m, 1H); MS [M-CF$_3$COO]$^+$: 438.

EXAMPLE 30

3(R)-(2-Furan-2-yl-2-hydroxy-2-thien-2-ylacetoxy)-1-(2-phenoxyethyl)-1-azoniabicyclo[2.2.2]octane; trifluoroacetate The title compound was synthesised as a mixture of diastereomers according to methods c and b. The yield of final step was 22 mg, 23%. $^1$H-NMR (DMSO-d6): δ 2.65-2.05 (m, 4H), 2.3 (m, 1H), 3.15-3.65 (m, 7H), 4.05 (m, 1H), 4.4 (m, 2H), 5.15 (m, 1H), 6.35 (dd, 1H), 6.45 (m, 1H), 6.95-7.05 (m, 4H), 7.15 (d, 1H), 7.3-7.4 (m, 3H), 7.5 (dd, 1H), 7.65 (d, 1H); MS [M-CF$_3$COO]$^+$: 454.

EXAMPLE 31

3(R)-(2-Furan-2-yl-2-hydroxy-2-thien-2-ylacetoxy)-1-(4-oxo-4-phenylbutyl)-1-azoniabicyclo[2.2.2]octane; trifluoroacetate The title compound was synthesised as a mixture of diastereomers according to methods c and b. The yield of final step was 15.4 mg, 15%. $^1$H-NMR (DMSO-d6): δ 1.65-2.1 (m, 6H), 7.05-7.55 (m, 9H), 3.95 (m, 1H), 5.1 (m, 1H), 6.35 (dd, 1H), 6.5 (m, 1H), 7.05 (m, 1H), 7.15 (m, 1H), 7.3 (d, 1H), 7.55 (m, 3H), 7.7 (dd, 2H), 8.0 (d, 2H); MS [M-CF$_3$COO]$^+$: 480.

EXAMPLE 32

1-(3-phenoxypropyl)-3(R)-(2-Furan-2-yl-2-hydroxy-2-thien-2-yl-acetoxy)-1-azoniabicyclo[2.2.2]octane; bromide The title compound was synthesised as a mixture of diastereomers according to methods c and a. The-yield of final step was 100 mg, 41%. $^1$H-NMR (DMSO-d6): δ 1.65-2.05 (m, 4H), 2.1-2.0 (m, 2H), 2.3 (m, 1H), 3.15 (m, 1H), 3.25-3.6 (6H), 3.9-4.1 (m, 3H), 5.1 (m, 1H), 6.35 (d, 1H), 6.45 (s, 1H), 6.95 (m, 3H), 7.05 (m, 1H), 7.2 (d, 1H), 7.3 (m, 3H), 7.55 (d, 1H), 7.7 (s, 1H); MS [M-Br]$^+$: 520; mp 173° C.

EXAMPLE 33

1-(3-phenoxypropyl)-3(R)-(2,2-difuran-2-yl-2-hydroxyacetoxy)-1-azoniabicyclo[2.2.2]octane; bromide The title compound was synthesised according to methods f and a. The yield of final step was 200 mg, 60%. $^1$H-NMR (DMSO-d6): δ 1.6-2.20 (m, 6H), 2.3 (m, 1H), 2.95-3.65 (m, 7H), 3.80-4.10 (m, 3H), 5.2 (m, 1H), 6.3-6.6 (m, 4H), 6.8-7.0 (m, 3H), 7.1 (s, OH), 7.3 (m, 2H), 7.7 (m, 2H); MS [M-Br]$^+$: 452.

EXAMPLE 34

3(R)-(2,2-Dithien-2-ylacetoxy)-1-(2-phenoxyethyl)-1-azoniabicyclo[2.2.2]octane; bromide The title compound was synthesised according to methods c and a. The yield of final step was 240 mg, 60%. $^1$H-NMR (DMSO-d6): δ 1.85-2.10 (m, 4H), 2.30 (s, 1H), 3.40 (m, 1H), 3.44-3.80 (m, 6H), 4.10 (m, 1H), 4.45 (m, 2H), 5.20 (m, 1H), 5.90 (s, 1H), 6.95-7.05 (m, 5H), 7.05-7.15 (m, 2H), 7.30-7.40 (m, 2H), 7.45 (m, 2H); MS [M-Br]$^+$: 454; mp 98° C.

EXAMPLE 35

3(R)-(2,2-Dithien-2-ylacetoxy)-1-(3-phenoxypropyl)-1-azoniabicyclo[2.2.2]octane; bromide The title compound was synthesised according to methods c and a. The yield of final step was 280 mg, 83%. $^1$H-NMR (DMSO-d6): δ 1.80-2.06 (m, 4H), 2.06-2.20 (m, 2H), 2.20-2.30 (m, 1H), 3.20-3.65 (m, 7H), 3.90-4.10 (m, 3H), 5.20 (m, 1H), 5.90 (s, 1H), 6.95-7.05 (m, 5H), 7.05-7.20 (m, 2H), 7.30-7.35 (m, 2H), 7.50 (m, 2H); MS [M-Br]$^+$: 468; mp 148° C.

EXAMPLE 36

3(R)-(2-Hydroxy-2,2-dithien-2-ylacetoxy)-1-phenethyl-1-azoniabicyclo[2.2.2]octane; bromide The title compound was synthesised according to methods c and a. The yield of final step was 180 mg, 59%. $^1$H-NMR (DMSO-d6): δ 1.65-2.0 (4H, m), 2.35 (m, 1H), 3.0 (m, 2H), 3.2-3.6 (m, 7H), 3.95 (m, 1H), 5.25 (m, 1H), 7.0 (m, 2H), 7.2 (m, 2H), 7.35 (m, 5H), 7.55 (m, 3H); MS [M-Br]$^+$: 454; mp 216° C.

EXAMPLE 37

3(R)-(2-Hydroxy-2,2-dithien-2-ylacetoxy)-1-(3-phenylpropyl)-1-azoniabicyclo[2.2.2]octane; bromide The title compound was synthesised according to methods c and a. The yield of final step was 450 mg, 58%. $^1$H-NMR (CDCl$_3$): δ 1.8-2.1 (m, 6H), 2.4 (m, 1H), 2.6 (m, 2H), 3.4-3.8 (m, 7H), 4.2 (m, 1H), 5.25 (m, 1H), 6.1 (bs, OH), 6.9 (m, 2H), 7.1-7.3 (m, 9H); MS [M-Br]$^+$: 468; mp 64° C.

EXAMPLE 38

3(R)-(2-Hydroxy-2,2-dithien-2-ylacetoxy)-1-(3-phenylallyl)-1-azoniabicyclo[2.2.2]octane; bromide The title compound was synthesised according to methods c and a. The yield of final step was 260 mg, 34%. $^1$H-NMR (CDCl$_3$): δ 1.8-2.05 (m, 4H), 2.4 (m, 1H), 3.55-3.95 (m, 5H), 4.15-4.5 (m, 3H), 5.25 (m, 1H), 5.9 (s, OH), 6.15 (m, 1H), 6.85 (t, 1H), 6.9-7.05 (m, 3H), 7.15 (m, 1H), 7.2-7.45 (m, 7H); MS [M-Br]$^+$: 466; mp 124° C.

EXAMPLE 39

3(R)-(2-Hydroxy-2,2-dithien-2-ylacetoxy)-1-(4-phenylbutyl)-1-azoniabicyclo[2.2.2]octane; bromide The title compound was synthesised according to methods c and a. The yield of final step was 320 mg, 40%. $^1$H-NMR (CDCl$_3$): δ 1.6-2.0 (m, 8H), 2.4 (m, 1H), 2.6 (m, 2H), 3.4-3.8 (m, 7H), 4.2 (m, 1H), 5.25 (m, 1H), 6.05 (bs, OH), 6.95 (m, 2H), 7.1-7.3 (m, 9H); MS [M-Br]$^+$: 482; mp 64° C.

EXAMPLE 40

3(R)-(2-Hydroxy-2,2-dithien-2-ylacetoxy)-1-(4-oxo-4-phenylbutyl)-1-azoniabicyclo[2.2.2]octane; trifluoroacetate The title compound was synthesised according to methods c and b. The yield of final step was 16 mg, 15%. $^1$H-NMR (DMSO-d6): δ 1.7-2.0 (m, 6H), 2.15 (m, 1H), 3.1 (t, 2H), 3.15-3.55 (m, 7H), 3.95 (m, 1H), 5.25 (m, 1H), 7.0 (d, 2H), 7.15 (d, 2H), 7.55 (m, 5H), 7.65 (t, 1H), 8.0 (d, 2H); MS[M-CF$_3$COO]$^+$: 496.

EXAMPLE 41

3(R)-(2-Hydroxy-2,2-dithien-2-ylacetoxy)-1-(3-phenylaminopropyl)-1-azoniabicyclo[2.2.2]octane; trifluoroacetate The title compound was synthesised according to methods c and b. The yield of final step was 14 mg, 14%. $^1$H-NMR (DMSO-d6): δ 1.7-2.0 (m, 5H), 2.3 (m, 1H), 3.0-3.5 (m, 9H), 3.9 (m, 1H), 5.25 (m, 1H), 5.65 (t, 1H), 6.55 (m, 3H), 7.0 (d, 2H), 7.1 (t, 2H), 7.15 (m, 2H), 7.5 (m, 3H); MS[M-CF$_3$COO]$^+$: 483.

EXAMPLE 42

3(R)-(2-Hydroxy-2,2-dithien-2-ylacetoxy)-1-[3-(methylphenylamino)propyl]-1-azoniabicyclo[2.2.2]octane; trifluoroacetate The title compound was synthesised according to methods c and b. The yield of final step was 20 mg, 19%. $^1$H-NMR (DMSO-d6): δ 1.65-2.0 (m, 6H), 2.9 (s, 3H), 3.1 (m, 1H), 3.2-3.45 (m, 8H), 3.95 (m, 1H), 5.2 (m, 1H), 6.65 (t, 1H), 6.75 (d, 2H), 7.0 (m, 2H), 7.2 (m, 4H), 7.5 (m, 3H); MS [M-CF$_3$COO]$^+$: 497.

EXAMPLE 43

3(R)-(2-Hydroxy-2,2-dithien-2-ylacetoxy)-1-(3-phenylsulfanylpropyl)-1-azoniabicyclo[2.2.2]octane; bromide The title compound was synthesised according to methods c and a. The yield of final step was 800 mg, 83%. $^1$H-NMR (DMSO-d6): δ 1.6-1.9 (m, 6H), 2.3 (m, 1H), 2.95 (t, 2H), 3.05 (m, 1H), 3.2-3.5 (m, 6H), 3.9 (m, 1H), 5.2 (m, 1H), 7.0 (m, 2H), 7.15 (m, 2H), 7.2 (m, 1H), 7.35 (m, 4H), 7.5 (m, 2H); MS [M-Br]$^+$: 500.

EXAMPLE 44

3(R)-(2-Hydroxy-2,2-dithien-2-ylacetoxy)-1-(3-phenoxypropyl)-1-azoniabicyclo[2.2.2]octane; bromide The title compound was synthesised according to methods c and a. The yield of final step was 490 mg, 90%. $^1$H-NMR (DMSO-d6): δ 1.7 (m, 2H), 1.95 (m, 2H), 2.1 (m, 2H), 2.3 (m, 1H), 3.2 (m, 1H), 3.45 (m, 6H), 4.0 (m, 3H), 5.15 (m, 1H), 6.9 (m, 3H), 7.0 (m, 2H), 7.2 (m, 2H), 7.3 (t, 2H), 7.5 (m, 3H); MS [M-Br]$^+$: 484; mp 227° C.

EXAMPLE 45

3(R)-(2-Hydroxy-2,2-dithien-2-ylacetoxy)-1-(3-o-tolyloxypropyl)-1-azoniabicyclo[2.2.2]octane; trifluoroacetate The title compound was synthesised according to methods c and b The yield of final step was 19 mg, 18%. $^1$H-NMR (DMSO-d6): δ 1.7-2.0 (m, 4H), 2.1-2.2 (m, 5H), 2.3 (m, 1H), 3.15-3.5 (m, 7H), 3.9-4.05 (m, 3H), 5.05 (m, 1H), 6.85 (t, 1H), 6.9 (d, 1H), 7.0 (m, 2H), 7.15 (m, 4H), 7.5 (m, 3H); MS [M-CF$_3$COO]$^+$: 498.

EXAMPLE 46

3-(R)-(2-Hydroxy-2,2-dithien-2-ylacetoxy)-1-[3-(2,4,6-trimethylphenoxy)propyl]-1-azoniabicyclo[2.2.2]octane; trifluoroacetate The title compound was synthesised according to methods c and b. The yield of final step was 22 mg, 20%. $^1$H-NMR (DMSO-d6): δ 1.7 (m, 2H), 1.95 (m, 2H), 2.1 (m, 2H), 2.2 (s, 9H), 2.35 (m, 1H), 3.2-3.5 (m, 7H), 3.7 (t, 2H), 3.95 (m, 1H), 5.25 (m, 1H), 6.8 (s, 2H), 7.0 (m, 2H), 7.2 (m, 2H), 7.5 (m, 3H); MS [M-CF$_3$COO]$^+$: 526.

EXAMPLE 47

1-[3-(2-tert-Butyl-6-methylphenoxy)propyl]-3(R)-(2-hydroxy-2,2-dithien-2-ylacetoxy)-1-azoniabicyclo[2.2.2]octane; trifluoroacetate The title compound was synthesised according to methods c and b. The yield of final step was 18 mg, 16%. $^1$H-NMR (DMSO-d6): δ 1.3 (s, 9H), 2.7 (m, 2H), 2.9 (m, 2H), 2.1 (m, 2H), 2.2 (s, 3H), 2.3 (m, 1H), 3.2-3.5 (m, 7H), 3.8 (t, 2H), 3.95 (m, 1H), 5.2 (m, 1H), 6.9-7.15 (m, 7H), 7.5 (m, 3H); MS [M-CF$_3$COO]$^+$: 554.

EXAMPLE 48

1-[3-(Biphenyl-4-yloxy)propyl]-3(R)-(2-hydroxy-2,2-dithien-2-ylacetoxy)-1-azoniabicyclo[2.2.2]-octane; trifluoroacetate The title compound was synthesised according to methods c and b. The yield of final step was 22 mg, 19%. $^1$H-NMR (DMSO-d6): δ 1.7 (m, 2H), 1.9 (m, 2H), 2.15 (m, 2H), 2.3 (m, 1H), 3.2-3.5 (m, 7H), 3.95 (m, 1H), 4.1 (t, 2H), 5.25 (m, 1H), 7.0 (m, 4H), 7.2 (m, 2H), 7.3 (t, 1H), 7.45 (t, 2H), 7.5 (m, 3H), 7.6 (m, 4H); MS [M-CF$_3$COO]$^+$: 560.

EXAMPLE 49

3(R)-(2-Hydroxy-2,2-dithien-2-ylacetoxy)-1-[3-(5,6,7,8-tetrahydronaphthalen-2-yloxy)-propyl]-1-azoniabicyclo[2.2.2]octane; trifluoroacetate The title compound was synthesised according to methods c and b. The yield of final step was 23 mg, 21%. $^1$H-NMR (DMSO-d6): δ 1.7 (m, 6H), 1.9-2.1 (m, 4H), 2.3 (m, 1H), 2.65 (m, 4H), 3.15-3.5 (m, 7H), 3.95 (m, 2H), 5.25 (m, 1H), 6.65 (m, 2H), 6.95 (d, 1H), 7.0 (m, 2H), 7.2 (m, 2H), 7.5 (m, 3H); MS [M-CF$_3$COO]$^+$: 538.

EXAMPLE 50

3(R)-(2-Hydroxy-2,2-dithien-2-ylacetoxy)-1-[3-(naphthalen-2-yloxy)propyl]-1-azoniabicyclo[2.2.2]octane; trifluoroacetate The title compound was synthesised according to methods c and b. The yield of final step was 17 mg, 15%. $^1$H-NMR (DMSO-d6): δ 1.7-2.0 (m, 4H), 2.1 (m, 1H), 2.35 (m, 1H), 3.15-3.35 (m, 7H), 3.95 (m, 1H), 4.17 (t, 2H), 5.25 (m, 1H), 7.0 (m, 2H), 7.15 (m, 3H), 7.35 (m, 2H), 7.5 (m, 4H), 7.85 (m, 3H); MS [M-CF$_3$COO]$^+$: 534.

EXAMPLE 51

3(R)-(2-Hydroxy-2,2-dithien-2-ylacetoxy)-1-[3-(naphthalen-1-yloxy)propyl]-1-azoniabicyclo[2.2.2]octane; trifluoroacetate The title compound has been described in method -b-.

EXAMPLE 52

1-[3-(2-Chlorophenoxy)propyl]-3(R)-(2-hydroxy-2,2-dithien-2-ylacetoxy)-1-azoniabicyclo[2.2.2]octane; trifluoroacetate The title compound was synthesised according to methods c and b. The yield of final step was 20 mg, 18%. $^1$H-NMR (DMSO-d6): δ 1.65-2.0 (m, 6H), 2.35 (m, 1H), 3.2 (m, 1H), 3.3-3.55 (m, 6H), 3.95 (m, 1H), 4.15 (t, 2H), 5.25 (m, 2H), 7.0 (m, 3H), 7.2 (m, 3H), 7.35 (t, 1H), 7.45 (d, 1H), 7.55 (m, 3H); MS [M-CF$_3$COO]$^+$: 519.

EXAMPLE 53

1-[3-(4-Fluorophenoxy)propyl]-3(R)-(2-hydroxy-2,2-dithien-2-ylacetoxy)-1-azoniabicyclo[2.2.2]octane; chloride The title compound was synthesised according to methods c and a. The yield of final step was 180 mg, 59%. $^1$H-NMR (DMSO-d6): δ 1.65-2.15 (m, 6H), 2.25 (m, 1H), 3.2 (m, 1H), 3.25-3.55 (m, 6H), 3.95 (m, 2H), 4.0 (t, 2H), 5.25 (m, 1H), 7.0 (m, 4H), 7.15 (m, 4H), 7.55 (m, 3H); MS [M-Cl]$^+$: 502; mp 160° C.

EXAMPLE 54

1-[3-(2,4-Difluorophenoxy)propyl]-3(R)-(2-hydroxy-2,2-dithien-2-ylacetoxy)-1-azoniabicyclo[2.2.2]octane; trifluoroacetate The title compound was synthesised according to methods c and b. The yield of final step was 14 mg, 13%. $^1$H-NMR (DMSO-d6): δ 1.65-2.0 (m, 4H), 2.15 (m, 2H), 2.35 (m, 1H), 3.2 (m, 1H), 3.25-3.35 (m, 6H), 3.95 (m, 1H), 4.1 (t, 2H), 5.15 (m, 1H), 7.05 (m, 3H), 7.2 (d, 2H), 7.25-7.35 (m, 2H), 7.55 (m, 3H); MS [M-CF$_3$COO]+: 520.

EXAMPLE 55

3(R)-(2-Hydroxy-2,2-dithien-2-ylacetoxy)-1-[3-(3-trifluoromethyl phenoxy)propyl]-1-azoniabicyclo[2.2.2]octane; trifluoroacetate The title compound was synthesised according to methods c and b. The yield of final step was 19 mg, 17%. $^1$H-NMR (DMSO-d6): δ 1.65-2.1 (m, 6H), 2.35 (m, 1H), 3.2 (m, 1H), 3.3-3.55 (m, 6H), 3.95 (m, 1H), 4.15 (t, 2H), 5.25 (m, 1H), 7.0 (m, 2H), 7.2 (m, 2H), 7.25-7.35 (m, 3H), 7.5-7.6 (m, 4H); MS [M-CF$_3$COO]$^+$: 552.

EXAMPLE 56

1-[3-(3-Cyanophenoxy)propyl]-3(R)-(2-hydroxy-2,2-dithien-2-ylacetoxy)-1-azoniabicyclo[2.2.2]octane; trifluoroacetate The title compound was synthesised according to methods c and b. The yield of final step was 18 mg, 17%. $^1$H-NMR (DMSO-d6): δ 1.65-2.1 (m, 6H), 2.35 (m, 1H), 3.2 (m, 1H), 3.3-3.55 (m, 6H), 3.95 (m, 1H), 4.15 (t, 2H), 5.25 (m, 1H), 7.0 (m, 2H), 7.18 (m, 2H), 7.3 (d, 1H), 7.45 (m, 2H), 7.55 (m, 4H); MS [M-CF$_3$COO]$^+$: 509.

EXAMPLE 57

1-[3-(4-Cyanophenoxy)propyl]-3(R)-(2-hydroxy-2,2-dithien-2-ylacetoxy)-1-azoniabicyclo[2.2.2]octane; bromide The title compound was synthesised according to methods c and a. The yield of final step was 180 mg, 53%. $^1$H-NMR (DMSO-d6): δ 1.65-2.2 (m, 6H), 2.3 (m, 1H), 3.2 (m, 1H), 3.3-3.55 (m, 6H), 3.95 (m, 1H), 4.15 (t, 2H), 5.25 (m, 1H), 7.0 (m, 2H), 7.1 (d, 2H), 7.15 (m, 2H), 7.5 (m, 2H), 7.8 (d, 2H); MS [M-Br]$^+$: 509; mp 158° C.

EXAMPLE 58

3(R)-(2-Hydroxy-2,2-dithien-2-ylacetoxy)-1-[3-(3-methoxyphenoxy)propyl]-1-azoniabicyclo[2.2.2]octane; trifluoroacetate The title compound was synthesised according to methods c and b. The yield of final step was 19 mg, 18%. $^1$H-NMR (DMSO-d6): δ 1.65-2.15 (m, 6H), 2.15 (m, 1H), 3.2 (m, 1H), 3.3-3.5 (m, 6H), 3.75 (s, 3H), 3.95 (m, 1H), 4.0 (t, 2H), 5.25 (m, 1H), 6.55 (m, 3H), 7.0 (m, 2H), 7.2 (m, 3H), 7.55 (m, 3H); MS [M-CF$_3$COO]$^+$: 514.

EXAMPLE 59

3(R)-(2-Hydroxy-2,2-dithien-2-ylacetoxy)-1-[3-(4-methoxyphenoxy)propyl]-1-azoniabicyclo[2.2.2]octane; trifluoroacetate The title compound was synthesised according to methods c and b. The yield of final step was 14 mg, 13%. $^1$H-NMR (DMSO-d6): δ 1.65-2.15 (m, 6H), 2.35 (m, 1H), 3.2 (m, 1H), 3.3-3.55 (m, 6H), 3.7 (s, 3H), 3.9-4.0 (m, 3H), 5.25 (m, 1H), 6.9 (s, 4H), 7.0 (m, 2H), 7.15 (m, 2H), 7.5 (m, 3H); MS [M-CF$_3$COO]$^+$: 514.

EXAMPLE 60

1-[3-(Benzo[1,3]dioxol-5-yloxy)propyl]-3(R)-(2-hydroxy-2,2-dithienn-2-ylacetoxy)-1-azoniabicyclo[2.2.2]octane; trifluoroacetate The title compound was synthesised according to methods c and b. The yield of final step was 19 mg, 17%. $^1$H-NMR (DMSO-d6): δ 1.65-2.15 (m, 7H), 2.3 (m, 1H), 3.15 (m, 1H), 3.25-3.5 (m, 6H), 3.9-4.0 (m, 3H), 5.25 (m, 1H), 5.95 (s, 2H), 6.4 (d, 1H), 6.65 (s, 1H), 6.85 (d, 1H), 7.0 (m, 2H), 7.2 (m, 2H), 7.5 (m, 3H); MS [M-CF$_3$COO]$^+$: 528.

EXAMPLE 61

1-[3-(2-Carbamoylphenoxy)propyl]-3(R)-(2-hydroxy-2,2-dithien-2-ylacetoxy)-1-azoniabicyclo[2.2.2]octane; trifluoroacetate The title compound was synthesised according to methods c and b. The yield of final step was 18 mg, 16%. $^1$H-NMR (DMSO-d6): δ 1.65-2.0 (m, 4H), 2.2 (m, 2H), 2.3 (m, 1H), 3.15 (m, 1H), 3.25-3.55 (m, 6H), 3.95 (m, 1H), 4.15 (t, 2H), 5.25 (m, 1H), 7.0-7.2 (m, 6H), 7.4-7.6 (m, 6H), 7.7 (d, 1H); MS [M-CF$_3$COO]$^+$: 527.

EXAMPLE 62

1-[3-(3-Dimethylaminophenoxy)propyl]-3(R)-(2-hydroxy-2,2-dithien-2-ylacetoxy)-1-azoniabicyclo[2.2.2]octane; trifluoroacetate The title compound was synthesised according to methods c and b. The yield of final step was 19 mg, 17%. $^1$H-NMR (DMSO-d6): δ 1.65-2.15 (m, 6H), 2.3 (m, 1H), 2.85 (s, 6H), 3.1-3.5 (m, 7H), 3.85-4.0 (m, 3H), 5.25 (m, 1H), 6.2 (m, 1H), 6.25 (d, 1H), 6.35 (d, 1H), 7.0 (m, 2H), 7.1 (t, 1H), 7.2 (m, 2H), 7.5 (m, 3H); MS [M-CF$_3$COO]$^+$: 527.

EXAMPLE 63

3(R)-(2-Hydroxy-2,2-dithien-2-ylacetoxy)-1-[3-(4-nitrophenoxy)propyl]-1-azoniabicyclo[2.2.2]octane; trifluoroacetate The title compound was synthesised according to methods c and b. The yield of final step was 22 mg, 20%. $^1$H-NMR (DMSO-d6): δ 1.65-2.0 (m, 4H), 2.2 (m, 2H), 2.3 (m, 1H), 3.2 (m, 1H), 3.3-3.5 (m, 6H), 3.95 (m, 1H), 4.2 (t, 2H), 5.25 (m, 1H), 7.0 (m, 2H), 7.15 (m, 4H), 7.5 (m, 3H), 8.15 (d, 2H); MS [M-CF$_3$COO]$^+$: 529.

EXAMPLE 64

3(R)-(2-Hydroxy-2,2-dithien-2-ylacetoxy)-1-[3-(3-nitrophenoxy)propyl]-1-azoniabicyclo[2.2.2]octane; trifluoroacetate The title compound was synthesised according to methods c and b. The yield of final step was 18 mg, 16%. $^1$H-NMR (DMSO-d6): δ 1.65-2.2 (m, 6H), 2.3 (m, 1H), 3.15-3.55 (m, 7H), 3.95 (m, 1H), 4.2 (t, 2H), 5.25 (m, 1H), 7.0 (m, 2H), 7.2 (m, 2H), 7.45 (dd, 1H), 7.55 (m, 3H), 7.6 (t, 1H), 7.75 (s, 1H), 7.85 (d, 1H); MS [M-CF$_3$COO]$^+$: 529.

EXAMPLE 65

1-[3-(4-Acetylaminophenoxy)propyl]-3(R)-(2-hydroxy-2,2-dithien-2-ylacetoxy)-1-azoniabicyclo[2.2.2]octane; trifluoroacetate The title compound was synthesised according to methods c and b. The yield of final step was 19 mg, 17%. $^1$H-NMR (DMSO-d6): δ 1.65-2.15 (m, 6H), 2.0 (s, 3H), 2.3 (m, 1H), 3.2 (m, 1H), 3.3-3.55 (m, 6H), 3.9-4.0 (m, 3H), 5.25 (m, 1H), 6.85 (d, 2H), 7.0 (m, 2H), 7.2 (m, 2H), 7.5 (m, 5H), 9.8 (s, 1H); MS [M-CF$_3$COO]$^+$: 541.

EXAMPLE 66

3(R)-(2-Hydroxy-2,2-dithien-2-ylacetoxy)-1-[3-(3-methoxycarbonylphenoxy)propyl]-1-azoniabicyclo[2.2.2]octane; trifluoroacetate The title-compound was synthesised according to methods c and b. The yield of final step was 18 mg, 16%. $^1$H-NMR (DMSO-d6): δ 1.65-2.2 (m, 6H), 2.3 (m, 1H), 3.2 (m, 1H), 3.3-3.5 (m, 6H), 3.85 (s, 3H), 3.95 (m, 1H), 4.1 (t, 2H), 5.25 (m, 1H), 7.0 (m, 2H), 7.15 (m, 2H), 7.25 (dd, 1H), 7.45-7.6 (m, 6H); MS [M-CF$_3$COO]$^+$: 542.

EXAMPLE 67

3(R)-(2-Hydroxy-2,2-dithien-2-ylacetoxy)-1-{3-[4-(3-hydroxypropyl)phenoxy]propyl}-1-azoniabicyclo[2.2.2]octane; trifluoroacetate The title compound was synthesised according to methods c and b. The yield of final step was 14 mg, 13%. $^1$H-NMR (DMSO-d6): δ 1.6-2.15 (m, 8H), 2.3 (m, 1H), 2.55 (t, 2H), 3.2 (m, 1H), 3.25-3.55 (m, 9H), 3.85-4.0 (m, 3H), 4.45 (t, OH), 5.25 (m, 1H), 7.85 (d, 2H), 7.0 (m, 2H), 7.1 (d, 2H), 7.15 (m, 2H), 7.5 (m, 2H); MS [M-CF$_3$COO]$^+$: 542.

EXAMPLE 68

3(R)-(2-Hydroxy-2,2-dithien-2-ylacetoxy)-1-[3-(2-hydroxymethylphenoxy)propyl]-1-azoniabicyclo[2.2.2]octane; trifluoroacetate The title compound was synthesised according to methods c and b. The yield of final step was 16 mg, 15%. $^1$H-NMR (DMSO-d6): δ 1.7-2.2 (m, 6H), 2.35 (m, 1H), 3.1-3.5 (m, 7H), 3.9-4.05 (m, 3H), 4.5 (m, 2H), 5.0 (t, OH), 5.15 (m, 1H), 6.9-7.05 (m, 4H), 7.2 (m, 2H), 7.4 (d, 1H), 7.5 (m, 3H); MS [M-CF$_3$COO]$^+$: 514.

EXAMPLE 69

3(R)-(2-Hydroxy-2,2-dithien-2-ylacetoxy)-1-[3-(3-hydroxymethylphenoxy)propyl]-1-azoniabicyclo[2.2.2]octane; trifluoroacetate The title compound was synthesised according to methods c and b. The yield of final step was 16 mg, 15%. $^1$H-NMR (DMSO-d6): δ 1.7-2.2 (m, 6H), 2.35 (m, 1H), 3.15-3.5 (m, 7H), 3.9 (m, 1H), 4.05 (t, 2H), 4.45 (d, 2H), 5.25 (m, 2H), 6.8 (d, 1H), 6.9 (m, 2H), 7.2 (m, 2H), 7.25 (t, 1H), 7.5 (m, 3H); MS [M-CF$_3$COO]$^+$: 514.

EXAMPLE 70

3(R)-(2-Hydroxy-2,2-dithien-2-ylacetoxy)-1-[3-(4-hydroxymethylphenoxy)propyl]-1-azoniabicyclo[2.2.2]octane; trifluoroacetate The title compound was synthesised according to methods c and b. The yield of final step was 17 mg, 16%. $^1$H-NMR (DMSO-d6) δ 1.65-2.2 (m, 6H), 2.3 (m, 1H), 3.15-3.55 (m, 7H), 3.9-4.05 (m, 3H), 4.4 (d, 2H), 5.1 (t, OH), 5.25 (t, 1H), 6.9 (d, 2H), 7.0 (m, 2H), 7.2 (m, 2H), 7.25 (d, 2H), 7.5 (m, 3H); MS [M-CF$_3$COO]$^+$: 514.

EXAMPLE 71

3(R)-(2-Hydroxy-2,2-dithien-2-ylacetoxy)-1-[3-(2-hydroxyphenoxy)propyl]-1-azoniabicyclo[2.2.2]octane; trifluoroacetate The title compound was synthesised according to methods c and b. The yield of final step was 24 mg, 19%. $^1$H-NMR (DMSO-d6): δ 1.65-2.15 (m, 6H), 2.35 (m, 1H), 3.2 (m, 1H), 3.25-3.55 (m, 6H), 3.95 (m, 1H), 4.0 (t, 2H), 5.25 (m, 1H), 6.7-6.85 (m, 3H), 6.95 (d, 1H), 7.0 (m, 2H), 7.2 (m, 2H), 7.5 (m, 3H), 8.85 (s, OH); MS [M-CF$_3$COO]$^+$: 500.

EXAMPLE 72

3(R)-(2-Hydroxy-2,2-dithien-2-ylacetoxy)-1-[3-(4-hydroxyphenoxy)propyl]-1-azoniabicyclo[2.2.2]octane; trifluoroacetate The title compound was synthesised according to methods c and b. The yield of final step was 16 mg, 15%. $^1$H-NMR (DMSO-d6): δ 1.65-2.1 (m, 6H), 2.3 (m, 1H), 3.2 (m, 1H), 3.25-3.5 (m, 6H), 3.95 (m, 3H), 5.25 (m, 1H), 6.7 (d, 2H), 6.75 (d, 2H), 7.0 (m, 2H), 7.2 (m, 2H), 7.5 (t, 3H), 9.0 (s, OH); MS [M-CF$_3$COO]$^+$: 500.

EXAMPLE 73

3(R)-(2-Hydroxy-2,2-dithien-2-ylacetoxy)-1-[3-(3-hydroxyphenoxy)propyl]-1-azoniabicyclo[2.2.2]octane; trifluoroacetate The title compound was synthesised according to methods c and b. The yield of final step was 16 mg, 15%. $^1$H-NMR (DMSO-d6): δ 1.65-2.15 (m, 6H), 2.3 (m, 1H), 3.2 (m, 1H), 3.3-3.55 (m, 6H), 3.9-4.0 (m, 3H), 5.25 (m, 1H), 6.9-6.0 (m, 3H), 7.0-7.1 (m, 3H), 7.2 (m, 2H), 7.5 (m, 3H), 9.45 (s, OH); MS [M-CF$_3$COO]$^+$: 500.

EXAMPLE 74

3(R)-(2-Hydroxy-2,2-dithien-2-ylacetoxy)-1-(3-pyrrol-1-ylpropyl)-1-azoniabicyclo[2.2.2]octane; trifluoroacetate The title compound was synthesised according to methods c and b. The yield of final step was 21 mg, 22%. $^1$H-NMR (DMSO-d6): δ 1.65-1.8 (m, 2H), 1.8-2.0 (m, 2H), 2.0-2.15 (m, 2H), 2.3 (m, 1H), 3.05-3.2 (m, 3H), 3.2-3.5 (m, 4H), 3.8-3.95 (m, 3H), 5.2 (m, 1H), 6.05 (t, 2H), 6.75 (t, 2H), 7.0 (t, 2H), 7.15 (d, 2H), 7.55 (m, 3H); MS [M-CF$_3$COO]$^+$: 457.

EXAMPLE 75

3(R)-(2-Hydroxy-2,2-dithien-2-ylacetoxy)-1-(4-oxo-4-thien-2-ylbutyl)-1-azoniabicyclo[2.2.2]octane; trifluoroacetate The title compound was synthesised according to methods c and b. The yield of final step was 18 mg, 17%. $^1$H-NMR (DMSO-d6): δ 1.7-1.85 (m, 2H), 1.9-2.1 (m, 4H), 2.3 (m, 1H), 3.1 (t, 2H), 3.15-3.55 (m, 7H), 3.95 (m, 1H), 5.25 (m, 1H), 7.0 (t, 2H), 7.4 (d, 2H), 7.25 (t, 1H), 7.55 (m, 3H), 7.95 (d, 1H), 8.05 (d, 1H); MS [M-CF$_3$COO]$^+$: 502.

EXAMPLE 76

3(R)-(2-Hydroxy-2,2-dithien-2-ylacetoxy)-1-[3-(1-methyl-[1H]-imidazol-2-ylsulfanyl)propyl]-1-azoniabicyclo[2.2.2]octane; trifluoroacetate The title compound was synthesised according to methods c and b. The yield of final step was 26 mg, 25%. $^1$H-NMR (DMSO-d6): δ 1.7 (m, 2H), 1.85-2.05 (m, 4H), 2.3 (m, 1H), 3.25-3.5 (m, 7H), 3.6 (s, 3H), 3.9 (m, 1H), 4.2 (t, 2H), 5.2 (m, 1H), 7.0 (m, 3H), 7.15 (m, 2H), 7.3 (m, 1H), 7.5 (m, 3H); MS [M-CF$_3$COO]$^+$: 504.

EXAMPLE 77

3(R)-(2-Hydroxy-2,2-dithien-2-ylacetoxy)-1-(2-thien-2-ylethyl)-1-azoniabicyclo[2.2.2]octane; bromide The title compound was synthesised according to methods c and a. The yield of final step was 430 mg, 54%. $^1$H-NMR (DMSO-d6): δ 1.6-1.8 (m, 2H), 2.3 (m, 1H), 3.15-3.3 (m, 4H), 3.35-3.55 (m, 5H), 3.95 (m, 1H), 5.25 (m, 1H), 7.0 (m, 4H), 7.15 (m, 2H), 7.4-7.5 (m, 4H); MS [M-Br]$^+$: 460; mp 206° C.

EXAMPLE 78

3(R)-(2-Hydroxy-2,2-dithien-2-ylacetoxy)-1-(3-thien-2-ylpropyl)-1-azoniabicyclo[2.2.2]octane; bromide The title compound was synthesised according to methods c and a. The yield of final step was 600 mg, 77%. $^1$H-NMR (DMSO-d6): δ 1.6-1.8 (m, 2H), 1.85-2.1 (m, 4H), 2.3 (m, 1H), 2.8 (t, 2H), 3.1-3.5 (m, 7H), 3.9 (m, 1H), 5.2 (m, 1H), 6.9-7.05 (m, 4H), 7.15 (m, 2H), 7.4 (d, 2H), 7.5 (m, 3H); MS [M-Br]$^+$: 474; mp 138° C.

EXAMPLE 79

1-[3-(Benzothiazol-2-yloxy)propyl]-3(R)-(2-hydroxy-2,2-dithien-2-ylacetoxy)-1-azoniabicyclo[2.2.2]octane; trifluoroacetate The title compound was synthesised according to methods c and b. The yield of final step was 23 mg, 21%. $^1$H-NMR (DMSO-d6): δ 1.65-2.1 (m, 6H), 2.3 (m, 1H), 3.15 (m, 1H), 3.25-3.5 (m, 6H), 3.85 (m, 1H), 4.0 (t, 2H), 5.2 (m, 1H), 7.0 (t, 2H), 7.15 (m, 2H), 7.25 (m, 1H), 7.45 (m, 5H), 7.7 (d, 1H); MS [M-CF$_3$COO]$^+$: 541.

EXAMPLE 80

1-(3-Benzyloxypropyl)-3(R)-(2-hydroxy-2,2-dithien-2-ylacetoxy)-1-azoniabicyclo[2.2.2]-octane; trifluoroacetate The title compound was synthesised according to methods c and b. The yield of final step was 16 mg, 15%. $^1$H-NMR (DMSO-d6): δ 1.65 (m, 2H), 1.9 (m, 4H), 2.3 (m, 1H), 3.1-3.4 (m, 7H), 3.5 (t, 2H), 3.9 (m, 1H), 3.9 (s, 2H), 5.2 (m, 1H), 7.0 (m, 2H), 7.15 (m, 2H), 7.35 (m, 5H), 7.5 (m, 3H); MS [M-CF$_3$COO]$^+$: 498.

EXAMPLE 81

3(R)-(2-Hydroxy-2,2-dithien-2-ylacetoxy)-1-[6-(4-phenylbutoxy) hexyl]-1-azoniabicyclo[2.2.2]octane; bromide The title compound was synthesised according to methods c and a. The yield of final step was 560 mg, 60%. $^1$H-NMR (CDCl$_3$): δ 1.2-1.75 (m, 16H), 1.8-2.1 (m, 4H), 2.4 (m, 1H), 2.6 (t, 2H), 3.3-3.75 (m, 11H), 4.2 (m, 1H), 5.3 (m, 1H), 6.0 (bs, OH), 6.95 (m, 2H), 7.15-7.3 (m, 9H); MS [M-Br]$^+$: 582.

EXAMPLE 82

3(R)-(2-Hydroxy-2,2-dithien-2-ylacetoxy)-1-(4-phenoxybutyl)-1-azoniabicyclo[2.2.2]octane; bromide The title compound was synthesised according to methods c and a. The yield of final step was 240 mg, 30%. $^1$H-NMR (DMSO-d6/CDCl$_3$): δ 1.8-1.95 (m, 6H), 2.1 (m, 2H), 2.45 (m, 1H), 3.18 (m, 1H), 3.5-3.8 (m, 6H), 4.0 (t, 2H), 4.15 (m, 1H) 5.15 (m, 1H), 6.7 (s, OH), 6.9 (m, 5H), 7.15 (d, 1H), 7.25 (m, 5H); MS [M-Br]$^+$: 498; mp 161° C.

EXAMPLE 83

3(R)-(2-Hydroxy-2,2-dithien-2-ylacetoxy)-1-(2-phenoxyethyl)-1-azoniabicyclo[2.2.2]octane; bromide The title compound was synthesised according to methods c and a. The yield of final step was 380 mg, 50%. $^1$H-NMR (DMSO-d6): δ 1.85 (m, 2H), 2.05 (m, 2H), 2.4 (m, 1H), 3.6-4.1 (m, 7H), 4.35 (m, 3H), 5.25 (m, 1H), 6.0 (bs, OH), 6.9 (m, 4H), 7.0 (t, 1H), 7.1 (dd, 2H), 7.2 (dd, 2H), 7.3 (t, 2H); MS [M-Br]$^+$: 470; mp 48° C.

EXAMPLE 84

1-(2-Benzyloxyethyl)-3(R)-(2-hydroxy-2,2-dithien-2-ylacetoxy)-1-azoniabicyclo[2.2.2]octane; trifluoroacetate The title compound was synthesised according to methods c and b. The yield of final step was 17 mg, 17%. $^1$H-NMR (DMSO-d6): δ 1.65-2.0 (m, 4H), 2.3 (m, 1H), 3.2-3.55 (m, 7H), 3.85 (m, 2H), 4.5 (s, 2H), 5.25 (m, 1H), 7.0 (t, 2H), 7.15 (t, 2H), 7.3-7.4 (m, 4H), 7.5 (m, 3H); MS [M-CF$_3$COO]$^+$: 484.

EXAMPLE 85

3(S)-(2-Hydroxy-2,2-dithien-2-ylacetoxy)-1-(3-phenoxypropyl)-1-azoniabicyclo[2.2.2]octane; bromide The title compound was synthesised according to methods c and a. The yield of final step was 600 mg, 54%. $^1$H-NMR (DMSO-d6/CDCl$_3$): δ 1.85-2.3 (m, 6H), 2.5 (m, 1H), 3.3 (m, 1H), 3.4 (d, 1H), 3.5-3.7 (m, 5H), 4.05 (t, 2H), 4.2 (m, 1H), 5.25 (m, 1H), 6.85 (d, 2H), 7.0 (m, 3H), 7.15 (m, 2H), 7.2 (d, 1H), 7.3 (m, 4H); MS [M-Br]$^+$: 484; mp 230° C.

EXAMPLE 86

4-(2-Hydroxy-2,2-dithien-2-ylacetoxy)-1-(3-phenoxypropyl)-1-azoniabicyclo[2.2.2]octane; bromide The title compound was synthesised according to methods f and a. The yield of final step was 290 mg, 60%. $^1$H-NMR (DMSO-d6): δ 2.15 (m, 2H), 2.35 (m, 6H), 3.35 (m, 2H), 3.65 (m, 6H), 4.05 (t, 2H), 6.9-7.05 (m, 5H), 7.1 (m, 2H), 7.3 (m, 3H), 7.55 (m, 2H); MS [M-Br]$^+$: 484; mp 1681 C.

EXAMPLE 87

4-(2-Hydroxy-2,2-dithien-2-yl-acetoxy)-1-phenethyl-1-azoniabicyclo[2.2.2]octane; bromide The title compound was synthesised according to methods f and a. The yield of final step was 260 mg, 57%. $^1$H-NMR (DMSO-d6): δ 2.35 (m, 6H), 3.0 (m, 2H), 3.4 (m, 2H), 3.75 (m, 6H), 7.0 (m, 2H), 7.3-7.5 (m, 6H), 7.55 (m, 2H); MS [M-Br]$^+$: 454; mp 1951 C.

EXAMPLE 88

1-(3-phenoxypropyl)-3(R)-(2,2-dithien-2-ylpropionyloxy)-1-azoniabicyclo[2.2.2]octane; bromide The title compound was synthesised according to methods c and a. The yield of final step was 390 mg, 92%. $^1$H-NMR (DMSO-d6): δ 1.65-2.20 (m, 6H), 2.10 (s, 3H), 2.30 (bs, 1H), 3.10 (m, 1H), 3.30-3.60 (m, 6H), 3.95-4.10 (m, 3H), 5.20 (m, 1H), 6.90-7.05 (m, 5H), 7.05-7.10 (m, 2H), 7.25-7.35 (m, 2H), 7.50 (m, 2H); MS [M-Br]$^+$: 482; mp 170° C.

EXAMPLE 89

3(R)-(2-Hydroxy-2,2-dithien-3-ylacetoxy)-1-(3-phenoxypropyl)-1-azoniabicyclo[2.2.2]octane; bromide The title compound was synthesised according to methods c and a. The yield of final step was 300 mg, 76%. $^1$H-NMR (DMSO-d6): δ 1.6 (m, 1H), 1.75 (m, 1H), 1.8-2.0 (m, 2H), 2.0-2.2 (m, 2H), 2.3 (m, 1H), 3.15 (m, 1H), 3.3-3.6 (m, 6H), 3.9 (m, 1H), 4.05 (t, 2H), 5.2 (m, 1H), 6.75 (s, OH), 6.95 (m, 3H), 7.15 (m, 2H), 7.3 (t, 2H), 7.4-7.5 (m, 4H); MS [M-Br]$^+$: 484; mp 2191 C.

EXAMPLE 90

3(R)-(2-Hydroxy-2,2-dithienyl-3-ylacetoxy)-1-(3-thien-2-ylpropyl)-1-azoniabicyclo[2.2.2]octane; bromide The title compound was synthesised according to methods c and a. The yield of final step was 300 mg, 77%. $^1$H-NMR (DMSO-d6): δ 1.5-1.6 (m, 1H), 1.6-1.75 (m, 1H), 1.8-2.1 (m, 4H), 2.25 (m, 1H), 2.8 (t, 2H), 3.05-3.5 (m, 7H), 3.8-3.95 (m, 1H), 5.15 (m, 1H), 6.75 (s, OH), 6.9-7.0 (m, 2H), 7.1 (m, 2H), 7.35-7.55 (m, 5H); MS [M-Br]$^+$: 474; mp 1921 C.

EXAMPLE 91

3(R)-(2-Hydroxy-2,2-dithien-3-yl-acetoxy)-1-phenethyl-1-azoniabicyclo[2.2.2]octane; trifluoroacetate The title compound was synthesised according to methods c and b. The yield of final step was 63 mg, 48%. $^1$H-NMR (DMSO-d6): δ 1.5-1.7 (m, 1H), 1.7-1.85 (m, 1H), 1.9-2.1 (m, 2H), 2.3 (m, 1H), 2.9-3.1 (m, 2H), 3.15-3.6 (m, 7H), 3.9-4.0 (m, 1H), 5.2 (m, 1H), 6.8 (s, OH), 7.1 (m, 2H), 7.25-7.35 (m, 5H), 7.4 (m, 2H), 7.5 (m, 2H); MS [M-CF3COO]$^+$: 454.

EXAMPLE 92

3(R)-(2-Hydroxy-2,2-dithien-3-yl-acetoxy)-1-(3-phenylpropyl)-1-azoniabicyclo[2.2.2]octane; trifluoroacetate The title compound was synthesised according to methods c and b. The yield of final step was 75 mg, 55%. $^1$H-NMR (DMSO-d6): δ 1.5-2.0 (m, 6H), 2.25 (m, 1H), 2.5-2.6 (m, 2H), 3.05-3.6 (m, 8H), 3.8-3.9 (m, 1H), 5.15 (m, 1H), 6.75 (s, OH), 7.1 (d, 2H), 7.2-7.35 (m, 5H), 7.4 (m, 2H), 7.5 (m, 2H); MS [M-CF3COO]$^+$: 468.

EXAMPLE 93

3(R)-(2-Hydroxy-2,2-dithien-3-ylacetoxy)-1-(4-phenylbutyl)-1-azoniabicyclo[2.2.2]octane; trifluoroacetate The title compound was synthesised according to methods c and b. The yield of final step was 68 mg, 48%. $^1$H-NMR (DMSO-d6): δ 1.5-1.8 (m, 6H), 1.8-2.0 (m, 2H), 2.25 (m, 1H), 2.6 (m, 2H), 3.05 (m, 1H), 3.15-3.45 (m, 6H), 3.85 (m, 1H), 5.15 (m, 1H), 6.75 (s, OH), 7.1 (d, 2H), 7.2 (m, 2H), 7.3 (m, 3H), 7.4 (m, 2H), 7.5 (m, 2H); MS [M-CF3COO]$^+$: 482.

EXAMPLE 94

3(R)-(2-Hydroxy-2,2-dithien-3-ylacetoxy)-1-(2-thien-2-ylethyl)-1-azoniabicyclo[2.2.2]octane; trifluoroacetate The title compound was synthesised according to methods c and b. The yield of final step was 65 mg, 49%. $^1$H-NMR (DMSO-d6): δ 1.5-1.65 (m, 1H), 1.65-1.78 (m, 1H), 1.85-2.05 (m, 2H), 2.3 (m, 1H), 3.1-3.6 (m, 9H), 3.95 (m, 1H), 5.2 (m, 1H), 6.75 (s, OH), 7.0 (m, 2H), 7.15 (m, 2H), 7.45 (m, 3H), 7.5 (m, 2H); MS [M-CF3COO]$^+$: 460.

EXAMPLE 95

3(R)-(2-Hydroxy-2,2-dithien-3-ylacetoxy)-1-(4-phenoxybutyl)-1-azoniabicyclo[2.2.2]octane; trifluoroacetate The title compound was synthesised according to methods c and b. The yield of final step was 63 mg, 43%. $^1$H-NMR (DMSO-d6): δ 1.5-2.0 (m, 8H), 2.3 (m, 1H), 3.1 (m, 1H), 3.2-3.5 (m, 6H), 3.85 (m, 1H), 4.0 (m, 2H), 5.2 (m, 1H), 6.75 (s, OH), 6.95 (m, 3H), 7.1 (d, 2H), 7.2 (m, 2H), 7.3 (t, 2H), 7.45 (m, 2H), 7.5 (m, 2H); MS [M-CF3COO]$^+$: 498.

EXAMPLE 96

3(R)-(2-Hydroxy-2,2-dithien-3-ylacetoxy)-1-(2-phenoxyethyl)-1-azoniabicyclo[2.2.2]octane; trifluoroacetate The title compound was synthesised according to methods c and b. The yield of final step was 72 mg, 52%. $^1$H-NMR (DMSO-d6): δ 1.55-1.65 (m, 1H), 1.7-1.8 (m, 1H), 1.85-2.05 (m,2H), 2.3 (m, 1H), 3.2-3.6 (m, 5H), 3.7 (m, 2H), 4.05 (m, 1H), 4.4 (m, 2H), 5.2 (m, 1H), 6.75 (s, OH), 6.95-7.05 (m, 3H), 7.1 (d, 2H), 7.3-7.5 (m, 6H); MS [M-CF3COO]$^+$: 470.

EXAMPLE 97

1-[3-(4-Fluorophenoxy)propyl]-3(R)-(2-hydroxy-2,2-dithien-3-ylacetoxy)-1-azoniabicyclo[2.2.2]octane; trifluoroacetate The title compound was synthesised according to methods c and b. The yield of final step was 79 mg, 54%. $^1$H-NMR (DMSO-d6): δ 1.55-1.65 (m, 1H), 1.7-1.8 (m, 1H), 1.85-2.0 (m, 2H), 2.05-2.2 (m, 2H), 2.3 (m, 1H), 3.1-3.2 (m, 1H), 3.25-3.55 (m, 6H), 3.85-3.95 (m, 1H), 4.0 (t, 2H), 5.2 (m, 1H), 6.75 (s, OH), 6.95 (m, 2H), 7.15 (m, 4H), 7.4 (m, 2H), 7.5 (m, 2H); MS [M-CF3COO]$^+$: 502.

EXAMPLE 98

3(R)-(2-Hydroxy-2,2-dithien-3-ylacetoxy)-1-(3-phenylallyl)-1-azoniabicyclo[2.2.2]octane; trifluoroacetate The title compound was synthesised according to methods c and b. The yield of final step was 24 mg, 17%. $^1$H-NMR (DMSO-d6): δ 1.8-2.05 (m, 4H), 2.3 (m, 1H), 3.15 (m, 1H), 3.3-3.5 (m, 4H), 3.9 (m, 1H), 4.05 (m 2H), 5.25 (m, 1H), 6.35 (m, 1H), 6.75 (s, OH), 6.85 (t, 1H), 7.1 (m, 2H), 7.3-7.5 (m, 5H), 7.55 (m, 4H); MS [M-CF3COO]$^+$: 502.

EXAMPLE 99

1-(3-phenylallyl)-3(R)-(9-Hydroxy-9[H]-fluorene-9-carbonyloxy)-1-azoniabicyclo[2.2.2]octane; bromide The title compound was synthesised according to methods c and a. The yield of final step was 400 mg, 93%. $^1$H-NMR (DMSO-d6): δ 1.35-1.50 (m, 1H), 1.60-1.75 (m, 1H), 1.75-1.95 (m, 2H), 2.10 (m, 1H), 2.85 (m, 1H), 3.10 (d, 1H), 3.20-3.50 (m, 3H), 3.85 (m, 1H), 4.0 (dd, 2H), 5.05 (m, 1H), 6.40 (dd, 1H), 6.80-6.90 (d, 1H), 6.85 (s, OH), 7.20-7.50 (m, 7H), 7.60 (m, 4H), 7.80 (m, 2H); MS [M-Br]$^+$: 452; mp 146° C.

EXAMPLE 100

3(R)-(9-Hydroxy-9[H]-fluorene-9-carbonyloxy)-1-(3-phenoxy-propyl)-1-azoniabicyclo[2.2.2]octane; bromide The title compound was synthesised according to methods c and a. The yield of final step was 690 mg, 83%. $^1$H-NMR (DMSO-d6): δ 1.47 (m, 1H), 1.68 (m, 1H), 1.87 (m, 2H), 2.1 (m, 3H), 2.89 (m, 1H), 3.15 (d, 1H), 3.4 (m, 5H), 3.9 (m, 1H), 4.0 (m, 2H), 5.04 (m, 1H), 6.85 (s, OH), 6.97 (m, 3H), 7.35 (m, 4H), 7.45 (m, 2H), 7.65 (m, 2H), 7.85 (m, 2H); MS [M-Br]$^+$: 470; mp 108° C.

EXAMPLE 101

3(R)-(9-Hydroxy-9[H]-fluorene-9-carbonyloxy)-1-phenethyl-1-azoniabicyclo[2.2.2]octane; bromide The title compound was synthesised according to methods c and a. The yield of final step was 170 mg, 74%. $^1$H-NMR (DMSO-d6): δ 1.45 (m, 1H), 1.65 (m, 1H), 1.85 (m, 2H), 2.1 (m, 1H), 2.9 (m, 3H), 3.15 (m, 1H), 3.3-3.5 (m, 5H), 3.85 (m, 1H), 5.05 (m, 1H), 6.85 (s, OH), 7.2-7.4 (m, 7H), 7.45 (t, 2H), 7.55 (d, 1H), 7.65 (d, 1H), 7.85 (d, 2H); MS [M-Br]$^+$: 440; mp 118° C.

EXAMPLE 102

3(R)-(9-Hydroxy-9[H]-fluorene-9-carbonyloxy)-1-(2-phenoxyethyl)-1-azoniabicyclo[2.2.2]octane; bromide The title compound was synthesised according to methods c and a. The yield of final step was 460 mg, 96%. $^1$H-NMR (DMSO-d6): δ 1.42 (m, 1H), 1.66 (m, 1H), 1.80-1.88 (m, 2H), 2.08 (m, 1H), 2.93 (m, 1H), 3.25-3.60 (m, 4H), 3.65 (m, 2H), 3.95 (m, 1H), 4.35 (m 2H), 5.02 (m, 1H), 6.85 (s, 1H, OH), 6.97 (d, 2H), 7.04 (t, 1H), 7.20-7.45 (m, 6H), 7.55-7.60 (t, 2H), 7.80 (d, 2H); MS [M-Br]$^+$: 456; mp 140° C.

EXAMPLE 103

3(R)-(9-Hydroxy-9[H]-fluorene-9-carbonyloxy)-1-(4-oxo-4-phenylbutyl)-1-azoniabicyclo[2.2.2]octane; trifluoroacetate The title compound was synthesised according to methods c and b. The yield of final step was 15 mg, 15%. $^1$H-NMR (DMSO-d6): δ 1.45 (m, 1H), 1.65 (m, 1H), 1.7-2.0 (m, 4H), 2.1 (m, 1H), 2.75 (m, 1H), 3.0-3.2 (m 4H), 3.25-3.4 (m, 4H), 3.85 (m, 1H), 5.05 (m, 1H), 6.85 (s, OH), 7.35 (t, 2H), 7.45 (t, 2H), 7.55-7.7 (m, 5H), 7.85 (d, 2H), 8.0 (d, 2H); MS [M-CF$_3$COO]$^+$: 482.

EXAMPLE 104

1-[3-(4-Fluorophenoxy)propyl]-3(R)-(9-hydroxy-9 [H]-fluorene-9-carbonyloxy)-1-azoniabicyclo[2.2.2] octane; chloride The title compound was synthesised according to methods c and a. The yield of final step was 440 mg, 94%. $^1$H-NMR (DMSO-d6): δ 1.4 (m, 1H), 1.65 (m, 2H), 1.7-1.95 (m, 2H), 2.0-2.1 (m, 3H), 2.8 (m, 1H), 3.1 (d, 1H), 3.2-3.4 (m, 5H), 3.8 (m, 1H), 4.0 (t, 2H), 5.0 (m, 1H), 6.85 (s, OH), 6.95 (m, 2H), 7.15 (t, 2H), 7.35 (t, 2H), 7.45 (t, 2H), 7.55 (d, 1H), 7.65 (d, 1H), 7.85 (d, 2H); MS [M-Br]$^+$: 488; mp 142° C.

EXAMPLE 105

1-[3-(2,4-Difluorophenoxy)propyl]-3(R)-(9-hydroxy-9[H]-fluorene-9-carbonyloxy)-1-azoniabicyclo[2.2.2]octane; trifluoroacetate The title compound was synthesised according to methods c and b. The yield of final step was 14 mg, 13%. $^1$H-NMR (DMSO-d6): δ 1.4 (m, 1H), 1.6-1.9 (m, 3H), 2.1 (m, 3H), 2.8 (m, 1H), 3.1 (d, 1H), 3.2-3.4 (m, 5H), 3.85 (m, 1H), 4.05 (t, 2H), 5.0 (m, 1H), 6.85 (s, OH), 7.05 (t, 1H), 7.15-7.4 (m, 4H), 7.45 (t, 2H), 7.55 (d, 1H), 7.65 (d, 1H), 7.85 (d, 2H); MS [M-CF$_3$COO]$^+$: 506.

EXAMPLE 106

3(R)-(9-Hydroxy-9[H]-fluorene-9-carbonyloxy)-1-(3-phenylaminopropyl)-1-azoniabicyclo[2.2.2]octane; trifluoroacetate The title compound was synthesised according to methods c and b. The yield of final step was 14 mg, 15%. $^1$H-NMR (DMSO-d6): δ 1.4 (m, 1H), 1.6 (m, 1H), 1.8 (m, 4H), 2.05 (m, 1H), 2.7 (m, 1H), 3.0 (m, 3H), 3.2-3.4 (m, 6H), 3.8 (m, 1H), 5.0 (m, 1H), 5.6 (t, NH), 6.55 (m, 3H), 6.85 (s, OH), 7.1 (t, 2H), 7.35 (dd, 2H), 7.45 (dd, 2H), 7.55 (dd, 2H), 7.8 (d, 2H); MS [M-CF$_3$COO]$^+$: 469.

EXAMPLE 107

3(R)-(9-Hydroxy-9[H]-fluorene-9-carbonyloxy)-1-[3-(4-hydroxyphenoxy)propyl]-1-azoniabicyclo[2.2.2]octane; trifluoroacetate The title compound was synthesised according to methods c and b. The yield of final step was 15 mg, 15%. $^1$H-NMR (DMSO-d6): δ 1.4 (m, 1H), 1.6 (m, 1H), 1.7-1.9 (m, 2H), 1.95-2.05 (m, 2H), 2.1 (m, 1H), 2.8 (m, 1H), 3.1 (d, 1H) 3.25-3.4 (m, 5H), 3.8-3.9 (m, 3H), 5.0 (m, 1H), 6.7 (d, 2H), 6.75 (d, 2H), 6.85 (s, OH), 7.35 (t, 2H), 7.45 (t, 2H), 7.55 (d, 1H), 7.65 (d, 1H), 7.85 (d, 2H), 9.0 (s, OH); MS [M-CF$_3$COO]$^+$: 486.

EXAMPLE 108

1-(2-Benzyloxyethyl)-3(R)-(9-hydroxy-9[H]-fluorene-9-carbonyloxy)-1-azoniabicyclo[2.2.2]octane; bromide The title compound was synthesised according to methods c and a. The yield of final step was 470 mg, 96%. $^1$H-NMR (DMSO-d6): δ 1.4 (m, 1H), 1.65 (m, 1H), 1.7-1.9 (m, 2H), 2.1 (m, 1H), 2.9 (m, 1H), 3.15-3.5 (m, 6H), 3.75 (m, 2H), 3.85 (m, 1H), 4.5 (s, 2H), 5.0 (m, 1H), 6.85 (s, OH), 7.3-7.5 (m, 9H), 7.55 (m, 2H), 7.8 (d, 2H); MS [M-Br]$^+$: 470; mp 86° C.

EXAMPLE 109

3(R)-(9-Hydroxy-9H-fluorene-9-carbonyloxy)-1-(3-thienyl-2-ylpropyl)-1-azoniabicyclo[2.2.2]octane; bromide The title compound was synthesised according to methods c and a. The yield of final step was 180 mg, 70%. $^1$H-NMR (DMSO-d6): δ 1.37 (m, 1H), 1.62 (m, 1H), 1.75-1.95 (m, 4H), 2.06 (m, 1H), 2.72 (m, 1H), 2.80 (m, 2H), 3.02-3.06 (m, 1H), 3.15-3.20 (m, 2H), 3.25-3.40 (m, 3H), 3.80 (m, 1H), 5.0 (m, 1H), 6.85 (s, 1H, OH), 6.95-7.0 (m, 2H), 7.25-7.50 (m, 5H), 7.55-7.65 (m, 2H), 7.85 (d, 2H); MS [M-Br]$^+$: 460; mp 140° C.

EXAMPLE 110

3(R)-(9-Hydroxy-9H-fluorene-9-carbonyloxy)-1-(3-phenylpropyl)-1-azoniabicyclo[2.2.2]octane; trifluoroacetate The title compound was synthesised according to methods c and b. The yield of final step was 80 mg, 40%. $^1$H-NMR (DMSO-d6) δ 1.35 (m, 1H), 1.6 (m, 1H), 1.7-1.90 (m, 2H), 2.05 (m, 1H), 2.5 (m, 2H), 2.7 (m, 1H), 3.0 (m, 1H), 3.15 (m, 2H), 3.2-3.4 (m, 3H), 3.75 (m, 1H), 5.0 (m, 1H), 6.85 (s, OH), 7.20-7.50 (m, 9H), 7.55 (dd, 2H), 7.85 (d, 2H); MS [M-CF3COO]$^+$: 454.

EXAMPLE 111

3(R)-(9-Hydroxy-9H-fluorene-9-carbonyloxy)-1-(4-phenylbutyl)-1-azoniabicyclo[2.2.2]octane; trifluoroacetate The title compound was synthesised according to methods c and b. The yield of final step was 74 mg, 35%. $^1$H-NMR (DMSO-d6): δ 1.35 (m, 1H), 1.45-1.65 (m, 5H), 1.7-1.90 (m, 2H), 2.05 (m, 1H), 2.55-2.75 (m, 3H), 3.0 (m, 1H), 3.15-3.45 (m, 5H), 3.75 (m, 1H), 5.0 (m, 1H), 6.85 (s, OH), 7.20 (m, 3H), 7.25-7.35 (m, 4H), 7.45-7.5 (m, 2H), 7.55-7.6 (dd, 2H), 7.85 (d, 2H); MS [M-CF3COO]$^+$: 468.

EXAMPLE 112

3(R)-(9-Hydroxy-9H-fluorene-9-carbonyloxy-1-(2-thienyl-2-ylethyl)-1-azoniabicyclo[2.2.2]octane; trifluoroacetate The title compound was synthesised according to methods c and b. The yield of final step was 79 mg, 39%. $^1$H-NMR (DMSO-d6): δ 1.4 (m, 1H), 1.65 (m, 1H), 1.8-1.95 (m, 2H), 2.1 (m, 1H), 2.9 (m, 1H), 3.1-3.25 (m, 4H), 3.15-3.45 (m, 5H), 3.85 (m, 1H), 5.05 (m, 1H), 6.85 (s, OH), 7.0 (m, 2H), 7.35 (t, 2H), 7.45-7.5 (m, 3H), 7.55 (d, 1H), 7.65 (d, 1H), 7.85 (d, 2H); MS[M-CF3COO]$^+$: 446.

EXAMPLE 113

3(R)-(9-Hydroxy-9H-fluorene-9-carbonyloxy)-1-(4-phenoxybutyl)-1-azoniabicyclo[2.2.2]octane; trifluoroacetate The title compound was synthesised according to methods c and b. The yield of final step was 72 mg, 33%. $^1$H-NMR (DMSO-d6): δ 1.4 (m, 1H), 1.55-1.9 (m, 7H), 2.05 (m, 1H), 2.7 (m, 1H), 3.0 (m, 1H), 3.15-3.5 (m, 7H), 3.8 (m, 1H), 4.0 (m, 2H), 5.05 (m, 1H), 6.85 (s, OH), 6.95 (m, 3H), 7.25-7.35 (m, 4H), 7.4-7.45 (m, 2H), 7.6 (dd, 2H), 7.85 (d, 2H); MS [M-CF3COO]$^+$: 484.

EXAMPLE 114

3(R)-(9-Methyl-9[H]-fluorene-9-carbonyloxy)-1-(3-phenylallyl)-1-azoniabicyclo[2.2.2]octane; bromide The title compound was synthesised according to methods c and a. The yield of final step was 200 mg, 76%. $^1$H-NMR (DMSO-d6): δ 1.54 (m, 1H), 1.70-1.86 (m, 3H), 1.76 (s, 3H), 2.13 (m, 1H), 3.06 (m, 1H), 3.20-3.50 (m, 4H), 3.86 (m, 1H), 4.05 (dd, 2H), 5.02 (m, 1H), 6.43 (dd, 1H), 6.86 (d, 1H), 7.26-7.46 (m, 7H), 7.58-7.65 (m, 3H), 7.70-7.72 (m, 1H), 7.87-7.90 (m, 2H); MS [M-Br]$^+$: 450; mp 234° C.

EXAMPLE 115

3(R)-(9-Methyl-9[H]-fluorene-9-carbonyloxy)-1-(2-phenoxyethyl)-1-azoniabicyclo[2.2.2]octane; bromide The title compound was synthesised according to methods c and a. The yield of final step was 210 mg, 66%. $^1$H-NMR (DMSO-d6): δ 1.55 (m, 1H), 1.60-2.0 (m, 3H), 1.76 (s, 3H), 2.12 (m, 1H), 3.10-3.25 (m, 1H), 3.40-3.80 (m, 6H), 4.0 (m, 1H), 4.41 (m, 2H), 4.98 (m, 1H), 6.98-7.05 (m, 3H), 7.27-7.46 (m, 6H), 7.63-7.71 (m, 2H), 7.87-7.90 (m, 2H); MS [M-Br]$^+$: 454; mp 202° C.

EXAMPLE 116

3(R)-(9-Methyl-9[H]-fluorene-9-carbonyloxy)-1-(3-phenoxypropyl)-1-azoniabicyclo[2.2.2]octane; bromide The title compound was synthesised according to methods c and a. The yield of final step was 210 mg, 61%. $^1$H-NMR (DMSO-d6): δ 1.55 (m, 1H), 1.60-2.0 (m, 3H), 1.78 (s, 3H), 2.0-2.20 (m, 3H), 3.0-3.10 (m, 1H), 3.25-3.53 (m, 6H), 3.86 (m, 1H), 4.03 (m, 2H), 4.98 (m, 1H), 6.95-7.0 (m, 3H), 7.30-7.48 (m, 6H), 7.65-7.92 (m, 4H); MS [M-Br]$^+$: 468; mp 204° C.

EXAMPLE 117

3(R)-(9-Methyl-9[H]-fluorene-9-carbonyloxy)-1-phenethyl-1-azoniabicyclo[2.2.2]octane; trifluoroacetate The title compound was synthesised according to methods c and b. The yield of final step was 18 mg, 19%. $^1$H-NMR (DMSO-d6): δ 1.55 (m, 1H), 1.65-1.95 (m, 3H), 1.75 (s, 3H), 2.15 (m, 1H), 2.9-3.1 (m, 4H), 3.25-3.55 (m, 5H), 3.85 (m, 1H), 5.05 (m, 1H), 7.25-7.55 (m, 9H), 7.65 (d, 1H), 7.75 (d, 1H), 7.95 (d, 2H); MS [M-CF$_3$COO]$^+$: 438.

EXAMPLE 118

3(R)-(9-Methyl-9[H]-fluorene-9-carbonyloxy)-1-(4-oxo-4-phenylbutyl)-1-azoniabicyclo[2.2.2]octane; trifluoroacetate The title compound was synthesised according to methods c and b. The yield of final step was 19 mg, 19%. $^1$H-NMR (DMSO-d6): δ 1.55 (m, 1H), 1.65-2.05 (m, 5H), 1.75 (s, 3H), 2.1 (m, 1H) 3.0 (m, 1H), 3.1-3.5 (m, 8H), 3.85 (m, 1H), 7.35-7.5 (m, 4H), 7.55 (t, 2H), 7.65 (t, 2H), 7.7 (d, 1H), 7.9 (d, 2H), 8.0 (d, 2H); MS [M-CF$_3$COO]$^+$: 480.

EXAMPLE 119

1-[3-(4-Fluorophenoxy)propyl]-3(R)-(9-methyl-9[H]-fluorene-9-carbonyloxy)-1-azoniabicyclo[2.2.2]octane; trifluoroacetate The title compound was synthesised according to methods c and b. The yield of final step was 23 mg, 23%. $^1$H-NMR (DMSO-d6): δ 1.55 (m, 1H), 1.65-1.95 (m, 3H), 1.75 (s, 3H), 2.05-2.15 (m, 3H), 3.0 (m, 1H), 3.25-3.5 (m, 6H), 3.85 (m, 1H), 4.0 (t, 2H), 5.0 (m, 1H), 6.95 (m, 2H), 7.15 (t, 2H), 7.35-7.5 (m, 4H), 7.65 (d, 1H), 7.75 (d, 1H), 7.9 (d, 2H); MS [M-CF$_3$COO]$^+$: 486.

EXAMPLE 120

1-[3-(2,4-Difluorophenoxy)propyl]-3(R)-(9-methyl-9H-fluorene-9-carbonyloxy)-1-azoniabicyclo[2.2.2]octane; trifluoroacetate The title compound was synthesised according to methods c and b. The yield of final step was 20 mg, 19%. $^1$H-NMR (DMSO-d6): δ 1.55 (m, 1H), 1.65-1.95 (m, 3H), 1.75 (s, 3H), 2.05-2.2 (m, 3H), 3.0 (m, 1H), 3.25-3.55 (m, 6H), 3.85 (m, 1H), 4.1 (t, 2H), 5.0 (m, 1H), 7.05 (t, 1H), 7.2-7.5 (m, 6H), 7.65 (d, 1H), 7.75 (d, 1H), 7.9 (d, 2H); MS [M-CF$_3$COO]$^+$: 504.

EXAMPLE 121

3(R)-(9-Methyl-9[H]-fluorene-9-carbonyloxy)-1-(3-phenylaminopropyl)-1-azoniabicyclo[2.2.2]octane; trifluoroacetate The title compound was synthesised according to methods c and b. The yield of final step was 19 mg, 19%. $^1$H-NMR (DMSO-d6): δ 1.55 (m, 1H), 1.65-1.95 (m, 5H), 1.75 (s, 3H), 2.1 (m, 1H), 2.95 (m, 1H), 3.05 (m, 2H), 3.15-3.45 (m, 6H), 3.8 (m, 1H), 5.0 (m, 1H), 5.65 (t, NH), 6.6 (m, 3H), 7.1 (t, 2H), 7.35-7.55 (m, 4H), 7.65 (d, 1H), 7.75 (d, 1H), 7.9 (d, 2H); MS [M-CF$_3$COO]$^+$: 467.

EXAMPLE 122

1-[3-(4-Hydroxyphenoxy)propyl]-3(R)-(9-methyl-9[H]-fluorene-9-carbonyloxy)-1-azoniabicyclo[2.2.2]octane; trifluoroacetate The title compound was synthesised according to methods c and b. The yield of final step was 22 mg, 22%. $^1$H-NMR (DMSO-d6): δ 1.55 (m, 1H), 1.65-1.9 (m, 3H), 1.75 (s, 3H), 2.0-2.15 (m, 3H), 3.0 (m, 1H), 3.25-3.5 (m, 6H), 3.8-3.95 (m, 3H), 5.0 (m, 1H), 6.7 (m, 2H), 6.75 (d, 1H), 7.35-7.45 (m, 4H), 7.65 (d, 1H), 7.75 (d, 1H), 7.9 (d, 2H), 9.0 (s, OH); MS [M-CF$_3$COO]$^+$: 484.

EXAMPLE 123

1-(2-Benzyloxyethyl)-3(R)-(9-methyl-9[H]-fluorene-9-carbonyloxy)-1-azoniabicyclo[2.2.2]octane; trifluoroacetate The title compound was synthesised according to methods c and b. The yield of final step was 17 mg, 17%. $^1$H-NMR (DMSO-d6): δ 1.55 (m, 1H), 1.65-1.95 (m, 4H), 1.75 (s, 3H), 2.15 (m, 1H), 3.1 (m, 1H), 3.3-3.55 (m, 6H), 3.8-3.95 (m, 3H), 4.5 (s, 2H), 5.0 (m, 1H), 7.3-7.5 (m, 9H), 7.6-7.7 (m, 2H), 7.9 (d, 2H); MS [M-CF$_3$COO]$^+$: 468.

EXAMPLE 124

3(R)-(9,10-Dihydroanthracene-9-carbonyloxy)-1-phenethyl-1-azoniabicyclo[2.2.2]octane; bromide The title compound was synthesised according to methods d and a. The yield of final step was 420 mg, 89%. $^1$H-NMR (DMSO-d6): δ 1.55 (m, 1H), 1.65-1.95 (m, 3H), 2.15 (m, 1H), 2.95 (m, 2H), 3.15 (m, 1H), 3.25-3.60 (m, 6H), 3.85 (m, 1H), 3.95-4.15 (dd, 2H, J1=1.8 Hz, J2=4.2 Hz), 5.02 (m, 1H), 5.25 (s, 1H), 7.25-7.43 (m, 11H), 7.48-7.55 (m, 2H); MS [M-Br]$^+$: 438; mp 216° C.

EXAMPLE 125

3(R)-(9,10-Dihydroanthracene-9-carbonyloxy)-1-(3-phenoxypropyl)-1-azoniabicyclo[2.2.2]octane; bromide The title compound was synthesised according to methods d and a. The yield of final step was 450 mg, 82%. $^1$H-NMR (DMSO-d6) δ 1.56 (m, 1H), 1.65-1.95 (m, 3H), 2.05-2.15 (m, 3H), 3.10 (m, 1H), 3.20-3.50 (m, 6H), 3.80 (m, 1H), 3.94-4.14 (m, 4H), 5.0 (m, 1H), 5.22 (s, 1H), 6.94-7.0 (m, 3H), 7.25-7.35 (m, 6H), 7.40 (m, 2H), 7.54-7.47 (m, 2H); MS [M-Br]$^+$: 468; mp 157° C.

EXAMPLE 126

1-(4-Phenylbutyl)-3(R)-(9[H]-xanthene-9-carbonyloxy)-azoniabicyclo[2.2.2]octane; bromide The title compound was synthesised according to methods d and a. The yield of final step was 83 mg, 21%. $^1$H-NMR (DMSO-d6): δ 1.50-2.0 (m, 8H), 2.15 (m, 1H), 2.65 (m, 2H), 3.05-3.65 (m, 7H), 3.80 (m, 1H), 5.0 (m, 1H), 5.30 (s, 1H), 7.10-7.45 (m, 11H), 7.45-7.60 (m, 2H); MS [M-Br]$^+$: 468; mp 95° C.

EXAMPLE 127

1-(2-Phenoxyethyl)-3(R)-(9[H]-xanthene-9-carbonyloxy)-1-azoniabicyclo[2.2.2]octane; bromide The title compound was synthesised according to methods d and a. The yield of final step was 300 mg, 73%. $^1$H-NMR (DMSO-d6): δ 1.70-2.0 (m, 4H), 2.2 (m, 1H), 3.20-3.80 (m, 7H), 4.0 (m, 1H), 4.40 (m, 2H), 5.05 (m, 1H), 5.30 (s, 1H), 7.0-7.10 (m, 7H), 7.30-7.45 (m, 4H), 7.45-7.55 (m, 2H); MS [M-Br]$^+$: 456; mp 200° C.

EXAMPLE 128

1-(3-Phenoxypropyl)-3(R)-(9[H]-xanthene-9-carbonyloxy)-1-azoniabicyclo[2.2.2]octane; bromide The title compound was synthesised according to methods d and a. The yield of final step was 350 mg, 83%. $^1$H-NMR (DMSO-d6): δ 1.70-2.0 (m, 4H), 2.0-2.25 (m, 3H), 3.15-3.65 (m, 7H), 3.85-3.95 (m, 1H), 3.95-4.10 (m, 2H), 5.0 (m, 1H), 5.30 (s, 1H), 6.90-7.0 (m, 3H), 7.10-7.25 (m, 4H), 7.25-7.40 (m, 4H), 7.40-7.60 (m, 2H); MS [M-Br]$^+$: 470; mp 184° C.

EXAMPLE 129

1-Phenethyl-3(R)-(9[H]-xanthene-9-carbonyloxy)-1-azoniabicyclo [2.2.2]octane; bromide The title compound was synthesised according to methods d and a. The yield of final step was 100 mg, 44%. $^1$H-NMR (DMSO-d6): δ 1.65-2.0 (m, 4H), 2.1 (m, 1H), 2.9-3.05 (m, 2H), 3.15-3.6 (m, 7H), 3.85 (m, 1H), 5.05 (m, 1H), 5.3 (s, 1H)), 7.15-7.55 (m, 13H); MS [M-Br]$^+$: 440.

EXAMPLE 130

1-(4-Oxo-4-phenylbutyl)-3(R)-(9[H]-xanthene-9-carbonyloxy)-1-azoniabicyclo[2.2.2]octane; trifluoroacetate The title compound was synthesised according to methods d and b. The yield of final step was 16 mg, 15%. $^1$H-NMR (DMSO-d6): δ 1.65-2.05 (m, 6H), 2.1 (m, 1H), 3.1-3.55 (m, 9H), 3.8 (m, 1H), 5.05 (m, 1H), 5.25 (s, 1H), 7.1-7.3 (m, 4H), 7.35 (t, 2H), 7.45-7.6 (m, 4H), 7.7 (d, 1H), 8.0 (d, 1H); MS [M-CF$_3$COO]$^+$: 482.

EXAMPLE 131

1-[3-(4-Fluorophenoxy)propyl]-3(R)-(9[H]-xanthene-9-carbonyloxy)-1-azoniabicyclo[2.2.2]octane, trifluoroacetate The title compound was synthesised according to methods d and b. The yield of final step was 18 mg, 18%. $^1$H-NMR (DMSO-d6): δ 1.7-2.1 (m, 6H), 2.15 (m, 1H), 3.1-3.5 (m, 7H), 3.8 (m, 1H), 4.0 (t, 2H), 5.0 (m, 1H), 5.3 (s, 1H), 6.95 (m, 2H), 7.1-7.3 (m, 6H), 7.4 (t, 2H), 7.5 (dd, 2H); MS [M-CF$_3$COO]$^+$: 488.

EXAMPLE 132

1-[3-(2,4-Difluorophenoxy)propyl]-3(R)-(9[H]-xanthene-9-carbonyloxy)-1-azoniabicyclo[2.2.2]octane; trifluoroacetate The title compound was synthesised according to methods d and b. The yield of final step was 14 mg, 14%. $^1$H-NMR (DMSO-d6): δ 1.65-1.95 (m, 4H), 2.05-2.2 (m, 3H), 3.1-3.55 (m, 7H), 3.8 (m, 1H), 4.05 (t, 2H), 5.0 (m, 1H), 5.3 (s, 1H), 7.05 (t, 1H), 7.1-7.55 (m, 10H); MS [M-CF$_3$COO]$^+$: 506.

EXAMPLE 133

1-(3-Phenylaminopropyl)-3(R)-(9[H]-xanthene-9-carbonyloxy)-1-azoniabicyclo[2.2.2]octane; trifluoroacetate The title compound was synthesised according to methods d and b. The yield of final step was 17 mg, 17%. $^1$H-NMR (DMSO-d6): δ 1.65-2.0 (m, 6H), 2.15 (m, 1H), 3.0-3.5 (m, 9H), 1.75 (m, 1H), 5.0 (m, 1H), 5.3 (s, 1H), 6.65 (t, NH), 6.55 (m, 3H), 0.5-7.3 (m, 6H), 7.35-7.55 (m, 4H); MS [M-CF$_3$COO]$^+$: 469.

EXAMPLE 134

1-[3-(4-Hydroxyphenoxy)propyl]-3(R)-(9[H]-xanthene-9-carbonyloxy)-1-azoniabicyclo[2.2.2]octane; trifluoroacetate The title compound was synthesised according to methods d and b. The yield of final step was 21 mg, 20%. $^1$H-NMR (DMSO-d6): δ 1.7-2.1 (m, 6H), 2.15 (m, 1H), 3.1-3.5 (m, 7H), 3.7-3.95 (m, 3H), 5.0 (m, 1H), 5.3 (s, 1H), 6.7 (d, 2H), 6.75 (d, 2H), 7.1-7.3 (m, 4H), 7.35-7.55 (m, 4H), 9.0 (s, OH); MS [M-CF$_3$COO]$^+$: 486.

EXAMPLE 135

1-(2-Benzyloxyethyl)-3(R)-(9[H]-xanthene-9-carbonyloxy)-1-azoniabicyclo[2.2.2]octane; trifluoroacetate The title compound was synthesised according to methods d and b. The yield of final step was 16 mg, 16%. $^1$H-NMR (DMSO-d6): δ 1.65-1.95 (m, 4H), 2.1 (m, 1H), 3.1-3.9 (m, 10H), 4.5 (s, 2H), 5.0 (m, 1H), 5.3 (s, 1H), 7.15 (m, 4H), 7.3-7.5 (m, 7H), 7.55 (t, 2H); MS [M-CF$_3$COO]$^+$: 470.

EXAMPLE 136

3(R)-(9-Hydroxy-9[H]-xanthene-9-carbonyloxy)-1-(3-phenoxypropyl)-1-azoniabicyclo[2.2.2]octane; bromide The title compound was synthesised according to methods c and a. The yield of final step was 340 mg, 71%. $^1$H-NMR (DMSO-d6): δ 1.30 (m, 1H), 1.65 (m, 1H), 1.70-1.95 (m, 2H), 1.95-2.10 (m, 3H), 2.70 (m, 1H), 2.90 (m, 1H), 3.2-3.5 (m, 5H), 3.80 (m, 1H), 4.0 (t, 2H), 5.05 (m, 1H), 6.90-7.0 (m, 3H), 7.20-7.35 (m, 7H), 7.40-7.46 (m, 2H), 7.65-7.70 (m, 2H); MS [M-Br]$^+$: 486; mp 219° C.

EXAMPLE 137

3(R)-(9-Hydroxy-9[H]-xanthene-9-carbonyloxy)-1-phenethyl-1-azoniabicyclo[2.2.2]octane; bromide The title compound was synthesised according to methods c and a. The yield of final step was 290 mg, 64%. $^1$H-NMR (DMSO-d6): δ 1.32 (m, 1H), 1.65 (m, 1H), 1.70-1.95 (m, 2H), 2.1 (m, 1H), 2.75-2.90 (m, 3H), 3.05 (m, 1H), 3.30-3.50 (m, 5H), 3.82 (m, 1H), 5.05 (m, 1H), 7.20-7.40 (m, 10H), 7.40-7.50 (m, 2H), 7.65-7.70 (m, 2H); MS [M-Br]$^+$: 456; mp 221° C.

EXAMPLE 138

3(R)-(9-Hydroxy-9H-xanthene-9-carbonyloxy)-1-(3-thien-2-ylpropyl)-1-azoniabicyclo[2.2.2]octane; bromide The title compound was synthesised according to methods c and a. The yield of final step was 310 mg, 97%. $^1$H-NMR (DMSO-d6): δ 1.30 (m, 1H), 1.62 (m, 1H), 1.70-1.90 (m, 4H), 2.05 (m, 1H), 2.60 (m, 1H), 2.75-2.85 (m, 4H), 3.15 (m, 2H), 3.25-3.40 (m, 2H), 3.75 (m,1H), 5.0 (m, 1H), 6.93 (m,1H) 7.0 (m, 1H), 7.14-7.26 (m, 5H), 7.36-7.45 (m, 3H), 7.63-7.67 (m, 2H); MS [M-Br]$^+$: 476; mp 111° C.

EXAMPLE 139

3(R)-(9-Hydroxy-9H-xanthene-9-carbonyloxy)-1-(3-phenylpropyl)-1-azoniabicyclo[2.2.2]octane; trifluoroacetate The title compound was synthesised according to methods c and b. The yield of final step was 85 mg, 41%. $^1$H-NMR (DMSO-d6): δ 1.30 (m, 1H), 1.65 (m, 1H), 1.70-1.95 (m, 2H), 2.05 (m, 1H), 2.5-2.6 (m, 2H), 2.80 (m, 1H), 3.05-3.75 (m, 7H), 5.05 (m, 1H), 7.1-7.45 (m, 12H), 7.65-7.70 (m, 2H); MS [M-CF3COO]$^+$: 470.

EXAMPLE 140

3(R)-(9-Hydroxy-9H-xanthene-9-carbonyloxy)-1-(4-phenylbutyl)-1-azoniabicyclo[2.2.2]octane; trifluoroacetate The title compound was synthesised according to methods c and b. The yield of final step was 84 mg, 38%. $^1$H-NMR (DMSO-d6): δ 1.30 (m, 1H), 1.4-1.85 (m, 7H), 2.05 (m, 1H), 2.5-2.6 (m, 2H), 2.80 (m, 1H), 3.05-3.4 (m, 6H), 3.7 (m, 1H), 5.05 (m, 1H), 7.15-7.35 (m, 10H), 7.4 (m, 1H), 7.65 (m, 2H); MS [M-CF3COO]$^+$: 484.

EXAMPLE 141

3(R)-(9-Hydroxy-9H-xanthene-9-carbonyloxy)-1-(2-thien-2-ylethyl)-1-azoniabicyclo[2.2.2]octane; trifluoroacetate The title compound was synthesised according to methods c and b. The yield of final step was 81 mg, 39%. $^1$H-NMR (DMSO-d6): δ 1.30 (m, 1H), 1.6 (m, 1H), 1.7-1.9 (m, 2H), 2.05 (m, 1H), 2.75 (m, 1H), 3.0 (m, 1H), 3.1-3.2 (m, 2H), 3.3-3.6 (m, 5H), 3.8 (m, 1H), 5.05 (m, 1H), 6.95-7.0 (m, 2H), 7.15-7.3 (m, 5H), 7.45 (m, 3H), 7.65 (m, 2H); MS [M-CF3COO]$^+$: 462.

EXAMPLE 142

3(R)-(9-Hydroxy-9H-xanthene-9-carbonyloxy)-1-(4-phenoxybutyl)-1-azoniabicyclo[2.2.2]octane; trifluoroacetate The title compound was synthesised according to methods c and b. The yield of final step was 83 mg, 37%. $^1$H-NMR (DMSO-d6): δ 1.3 (m, 1H), 1.5-1.9 (m, 7H), 2.05 (m, 1H), 2.6 (m, 1H), 2.8 (m, 1H), 3.1-3.45 (m, 7H), 3.75 (m, 1H), 4.0 (m, 2H), 5.05 (m, 1H), 6.95-7.0 (m, 3H), 7.15-7.45 (m, 9H), 7.65 (m, 2H); MS [M-CF3COO]$^+$: 500.

EXAMPLE 143

3(R)-(9-Hydroxy-9H-xanthene-9-carbonyloxy)-1-(2-phenoxyethyl)-1-azoniabicyclo[2.2.2]octane; trifluoroacetate The title compound was synthesised according to methods c and b. The yield of final step was 102 mg, 48%. $^1$H-NMR (DMSO-d6): δ 1.3 (m, 1H), 1.55-1.95 (m, 3H), 2.05 (m, 1H), 2.8 (m, 1H), 3.1 (m, 1H), 3.35-3.65 (m, 5H), 3.9 (m, 1H), 4.35 (m, 2H), 5.05 (m, 1H), 6.95 (d, 2H), 7.0-7.1 (m, 2H), 7.2 (m, 4H), 7.3-7.45 (m, 4H), 7.6 (t, 2H); MS [M-CF3COO]$^+$: 472.

EXAMPLE 144

1-[3-(4-Fluorophenoxy)propyl]-3(R)-(9-hydroxy-9H-xanthene-9-carbonyloxy)-1-azoniabicyclo[2.2.2]octane; trifluoroacetate The title compound was synthesised according to methods c and b. The yield of final step was 99 mg, 44%. $^1$H-NMR (DMSO-d6): δ 1.3 (m, 1H), 1.6 (m, 1H), 1.7-2.0 (m, 4H), 2.05 (m, 1H), 2.7 (m, 1H), 2.9 (m, 1H), 3.2-3.5 (m, 5H), 3.75-3.85 (m, 1H), 3.95 (m, 2H), 5.0 (m, 1H), 6.95 (m, 2H), 7.1-7.3 (m, 7H), 7.45 (t, 2H), 7.65 (t, 2H); MS [M-CF3COO]$^+$: 504.

EXAMPLE 145

3(R)-(9-Hydroxy-9H-xanthene-9-carbonyloxy)-1-(3-phenylallyl)-1-azoniabicyclo[2.2.2]octane; trifluoroacetate The title compound was synthesised according to methods c and b. The yield of final step was 25 mg, 12%. $^1$H-NMR (DMSO-d6): δ 1.25-1.30 (m, 1H), 1.55-1.95 (m, 3H), 2.10 (m, 1H), 2.65-2.75 (m, 1H), 2.9 (m, 1H), 3.25-3.50 (m, 2H), 3.75-3.8 (m, 1H), 3.95 (m, 2H), 4.2 (d, 1H), 5.0 (m, 1H), 6.35 (m, 1H), 6.80 (d, 1H), 7.05-7.50 (m, 8H), 7.60 (m, 4H); MS [M-CF3COO]$^+$: 468.

EXAMPLE 146

3(R)-(9-Methyl-9[H]-xanthene-9-carbonyloxy)-1-(3-phenoxypropyl)-1-azoniabicyclo[2.2.2]octane; bromide The title compound was synthesised according to methods c and a. The yield of final step was 110 mg. $^1$H-NMR (DMSO-d6): δ 1.4 (m, 1H), 1.65 (m, 1H), 1.75-1.95 (m, 2H), 1.9 (s, 3H), 2.05-2.15 (m, 3H), 1.8 (m, 1H), 3.15 (m, 2H), 3.25-3.5 (m, 5H), 3.85 (m, 1H), 4.0 (t, 2H), 5.05 (m, 1H), 6.95-7.0 (m, 3H), 7.15-7.2 (m, 4H), 7.3-7.4 (m, 4H), 7.45 (d, 1H), 7.55 (d, 1H); MS [M-Br]$^+$: 484; mp 195° C.

EXAMPLE 147

3(R)-(9-Methyl-9[H]-xanthene-9-carbonyloxy)-1-phenethyl-1-azoniabicyclo[2.2.2]octane; trifluoroacetate The title compound was synthesised according to methods c and b. The yield of final step was 19 mg, 20%. $^1$H-NMR (DMSO-d6): δ 1.4 (m, 1H), 1.65 (m, 1H), 1.8-1.95 (m, 2H), 1.9 (s, 3H), 2.15 (m, 1H), 2.8-2.95 (m, 3H), 3.15 (d, 1H), 3.3-3.5 (m, 5H), 4.9 (m, 1H), 5.1 (m, 1H), 7.15 (m, 4H), 7.25-7.4 (m, 7H), 7.45 (d, 1H), 7.55 (d, 1H); MS [M-CF$_3$COO]$^+$: 454.

EXAMPLE 148

3(R)-(9-Methyl-9[H]-xanthene-9-carbonyloxy)-1-(2-phenoxyethyl)-1-azoniabicyclo[2.2.2]octane; trifluoroacetate The title compound was synthesised according to methods c and b. The yield of final step was 24 mg, 24%. $^1$H-NMR (DMSO-d6): δ 1.4 (m, 1H), 1.65 (m, 1H), 1.8-1.95 (m, 2H), 1.9 (s, 3H), 2.15 (m, 1H), 2.95 (m, 1H), 3.25 (m, 1H), 3.4-3.65 (m, 5H), 3.85 (m, 1H), 4.35 (t, 2H), 5.05 (m, 1H), 6.95 (d, 2H), 7.05 (t, 2H), 7.15 (m, 3H), 7.25-7.45 (m, 6H); MS [M-CF$_3$COO]$^+$: 470.

EXAMPLE 149

3(R)-(9-Methyl-9[H]-xanthene-9-carbonyloxy)-1-(4-oxo-4-phenylbutyl)-1-azoniabicyclo[2.2.2]octane; trifluoroacetate The title compound was synthesised according to methods c and b. The yield of final step was 19 mg, 19%. $^1$H-NMR (DMSO-d6): δ 1.4 (m, 1H), 1.65 (m, 1H), 1.75-1.95 (m, 7H), 2.15 (m, 1H), 2.8 (m, 1H), 3.05-3.25 (m, 4H), 3.3-3.5 (m, 4H), 3.85 (m, 1H), 5.05 (m, 1H), 7.15 (m, 4H), 7.35 (t, 2H), 7.45-7.6 (m, 4H), 7.7 (t, 1H), 8.0 (d, 2H); MS [M-CF$_3$COO]$^+$: 496.

EXAMPLE 150

1-[3-(4-Fluorophenoxy)propyl]-3(R)-(9-methyl-9[H]-xanthene-9-carbonyloxy)-1-azoniabicyclo[2.2.2]octane; trifluoroacetate The title compound was synthesised according to methods c and b. The yield of final step was 25 mg, 24%. $^1$H-NMR (DMSO-d6): δ 1.4 (m, 1H), 1.65 (m, 1H), 1.75-1.95 (m, 2H), 1.9 (s, 3H), 1.95-2.1 (m, 2H), 2.15 (m, 1H), 2.8 (m, 1H), 3.1 (d, 1H), 3.25-3.5 (m, 5H), 3.8 (m, 1H), 4.0 (t, 2H), 5.05 (m, 1H), 6.95 (m, 2H), 7.15 (m, 6H), 7.35 (t, 2H), 7.5 (dd, 2H); MS [M-CF$_3$COO]$^+$: 502.

EXAMPLE 151

1-[3-(2,4-Difluorophenoxy)propyl]-3(R)-(9-methyl-9[H]-xanthene-9-carbonyloxy)-1-azoniabicyclo[2.2.2]octane; trifluoroacetate The title compound was synthesised according to methods c and b. The yield of final step was 16 mg, 15%. $^1$H-NMR (DMSO-d6): δ 1.4 (m, 1H), 1.65 (m, 1H), 1.75-1.95 (m, 2H), 1.9 (s, 3H), 2.0-2.15 (m, 3H), 2.8 (m, 1H), 3.1 (d, 1H), 7.05 (t, 1H), 7.1-7.4 (m, 8H), 7.5 (dd, 2H); MS [M-CF$_3$COO]$^+$: 520.

EXAMPLE 152

3(R)-(9-Methyl-9[H]-xanthene-9-carbonyloxy)-1-(3-phenylaminopropyl)-1-azoniabicyclo[2.2.2]octane; trifluoroacetate The title compound was synthesised according to methods c and b. The yield of final step was 16 mg, 15%. $^1$H-NMR (DMSO-d6): δ 1.35 (m, 1H), 1.6 (m, 1H), 1.7-1.9 (m, 4H), 1.9 (s, 3H), 2.1 (m, 1H), 2.7 (m, 1H), 2.95-3.05 (m, 3H), 3.1-3.4 (m, 6H), 3.75 (m, 1H), 5.0 (m, 1H), 5.6 (m, 1H), 6.55 (m, 3H), 7.05-7.15 (m, 6H), 7.3 (m, 2H), 7.45 (t, 2H); MS [M-CF$_3$COO]$^+$: 483.

EXAMPLE 153

1-[3-(4-Hydroxyphenoxy)propyl]-3(R)-(9-methyl-9 [H]-xanthene-9-carbonyloxy)-1-azoniabicyclo[2.2.2] octane; trifluoroacetate The title compound was synthesised according to methods c and b. The yield of final step was 19 mg, 18%. $^1$H-NMR (DMSO-d6): δ 1.4 (m, 1H), 1.65 (m, 1H), 2.75-2.05 (m, 4H), 1.9 (s, 3H), 2.15 (m, 1H), 2.8 (m, 1H), 3.1 (d, 1H), 3.25-3.5 (m, 5H), 3.8-3.95 (m, 3H), 5.05 (m, 1H), 6.65-6.8 (m, 4H), 7.2 (m, 4H), 7.35 (t, 2H), 7.5 (m, 2H), 9.0 (s, OH); MS [M-CF$_3$COO]$^+$: 500.

EXAMPLE 154

1-(2-Benzyloxyethyl)-3(R)-(9-methyl-9[H]-xanthene-9-carbonyloxy)-1-azoniabicyclo[2.2.2]octane; trifluoroacetate The title compound was synthesised according to methods c and b. The yield of final step was 14 mg, 14%. $^1$H-NMR (DMSO-d6): δ 1.4 (m, 1H), 1.65 (m, 1H), 1.75-1.95 (m, 2H), 1.9 (s, 3H), 2.1 (m, 1H), 2.9 (m, 1H), 3.2-3.5 (m, 6H), 3.75-3.95 (m, 3H), 4.5 (s, 2H), 5.05 (m, 1H), 7.15 (m, 4H), 7.3-7.5 (m, 9H); MS [M-CF$_3$COO]$^+$: 484.

EXAMPLE 155

1-(3-Phenoxypropyl)-3(R)-(9[H]-thioxanthene-9-carbonyloxy)-1-azonia-bicyclo[2.2.2]octane; bromide The title compound was synthesised according to methods d and a. The yield of final step was 323 mg, 50%. $^1$H-NMR (DMSO-d6): δ 1.35 (m, 1H), 1.65 (m, 1H), 1.70-1.95 (m, 2H), 2.0-2.2 (m, 3H), 2.75-2.90 (m, 1H), 3.12 (m, 1H), 3.25-3.50 (m, 5H), 3.80 (m, 1H), 4.0 (t, 2H), 5.0 (m, 1H), 5.6 (s, 1H), 6.94-7.0 (m, 3H), 7.22-7.41 (m, 6H), 7.45-7.64 (m, 4H); MS [M-Br]$^+$: 486; mp 157° C.

EXAMPLE 156

1-(3-phenylallyl)-3(R)-(10,11-Dihydro-5H-dibenzo [a,d]cycloheptene-5-carbonyloxy)-1-azoniabicyclo [2.2.2]octane; bromide The title compound was synthesised according to methods d and a. The yield of final step was 250 mg, 94%. $^1$H-NMR (CDCl$_3$): δ 1.50-1.60 (m, 1H), 1.60-1.80 (m, 1H), 1.90 (m, 2H), 2.30 (m, 1H), 2.65-2.80 (m, 2H), 2.90-3.20 (m, 3H), 3.50 (d, 1H), 3.60-3.90 (m, 3H), 4.20 (m, 1H), 4.35-4.60 (double dd, 2H), 5.10 (m, 1H), 5.15 (s, 1H), 6.05 (dd, 1H), 6.90-7.0 (m, 2H), 7.0-7.5 (m, 11H); MS [M-Br]$^+$: 464; mp 132° C.

EXAMPLE 157

1-(3-phenoxypropyl)-3(R)-(10,11-Dihydro-5H-dibenzo[a,d]cycloheptene-5-carbonyloxy)-1-azoniabicyclo[2.2.2]octane; bromide The title compound was synthesised according to methods d and a. The yield of final step was 290 mg, 94%. $^1$H-NMR (CDCl$_3$): δ 1.45-1.60 (m, 1H), 1.65-1.80 (m, 1H), 1.80-2.0 (m, 2H), 2.0-2.20 (m, 3H), 2.80-3.0 (m, 3H), 3.15-3.30 (m, 2H), 3.30-3.45 (d, 1H), 3.45-3.80 (m, 5H), 3.85-4.0 (m, 2H), 4.20 (m, 1H), 5.10 (m, 1H), 5.20 (s, 1H), 6.80-6.90 (d, 2H), 6.90-7.0 (t, 1H), 7.10-7.30 (m, 8H), 7.40 (m, 2H); MS [M-Br]$^+$: 482; mp 182° C.

EXAMPLE 158

3(R)-(5[H]-Dibenzo[a,d]cycloheptene-5-carbonyloxy)-1-(3-phenoxypropyl)-1-azoniabicyclo[2.2.2] octane; bromide The title compound was synthesised according to methods d and a. The yield of final step was 180 mg, 56%. $^1$H-NMR (DMSO-d6) δ 1.2 (m, 1H), 1.6 (m, 1H), 1.7-1.9 (m, 2H), 1.95 (m, 1H), 2.1 (m, 2H), 2.8 (m, 1H), 2.95 (d, 1H), 3.25-3.45 (m, 5H), 3.8 (m, 1H), 4.05 (t, 2H), 4.9 (m, 1H), 5.45 (s, 1H), 6.9-7.1 (m, 5H), 7.3-7.5 (m, 9H), 7.55 (d, 2H); MS [M-Br]$^+$: 480; mp 1111 C.

EXAMPLE 159

3(R)-(5[H]-Dibenzo[a,d]cycloheptene-5-carbonyloxy)-1-phenethyl-1-azoniabicyclo[2.2.2]octane; bromide The title compound was synthesised according to methods d and a. The yield of final step was 210 mg, 68%. $^1$H-NMR (DMSO-d6): δ 1.2 (m, 1H), 1.7-1.9 (m, 2H), 2.0 (m, 1H), 2.85-3.1 (m, 4H), 3.3-3.5 (m, 5H), 3.85 (m, 1H), 4.95 (m, 1H), 5.45 (s, 1H), 7.05 (m, 2H), 7.25-7.5 (m, 11H), 7.55 (m, 2H); MS [M-Br]$^+$: 450; mp 2481 C.

The Examples 160 to 164 illustrate pharmaceutical compositions according to the present invention and procedure for their preparation.

EXAMPLE 160

Preparation of a Pharmaceutical Composition: Tablets

Formulation:

| | |
|---|---|
| Compound of the present invention | 5.0 mg |
| Lactose | 113.6 mg |
| Macrocrystalline cellulose | 28.4 mg |
| Light silicic anhydride | 1.5 mg |
| Magnesium stearate | 1.5 mg |

Using a mixer machine, 15 g of the compound of the present invention was mixed with 340.8 g of lactose and 85.2 g of microcrystalline cellulose. The mixture was subjected to compression moulding using a roller compactor to give a flake-like compressed material. The flake-like compressed material was pulverized using a hammer mill, and the pulverized material was screened through a 20 mesh screen. A 4.5 g portion of light silicon anhydride and 4.5 g of magnesium stearate were added to the screened material and mixed. The mixer product was subjected to a tablets making machine equipped with a die/punch system of 7.5 mm in diameter, thereby obtaining 3,000 tablets each having 150 mg in weight.

EXAMPLE 161

Preparation of a Pharmaceutical Composition:
Tablets Coated

Formulation:

| Compound of the present invention | 5.0 mg |
| Lactose | 95.2 mg |
| Corn starch | 40.8 mg |
| Polyvinylpyrrolidone K25 | 7.5 mg |
| Magnesium stearate | 1.5 mg |
| Hydroxypropylcellulose | 2.3 mg |
| Polyethylene glycol 6000 | 0.4 mg |
| Titanium dioxide | 1.1 mg |
| Purified talc | 0.7 mg |

Using a fluidized bed granulating machine, 15 g of the compound of the present invention was mixed with 285.6 g of lactose and 122.4 g of corn starch. Separately, 22.5 g of polyvinylpyrrolidone was dissolved in 127.5 g of water to prepare a binding solution. Using a fluidized bed granulating machine, the binding solution was sprayed on the above mixture to give granulates. A 4.5 g portion of magnesium stearate was added to the obtained granulates and mixed. The obtained mixture was subjected to a tablet making machine equipped with a die/punch biconcave system of 6.5 mm in diameter, thereby obtaining 3,000 tablets, each having 150 mg in weight.

Separately, a coating solution was prepared by suspending 6.9 g of hydroxypropylmethylcellulose 2910, 1.2 g of polyethylene glycol 6000, 3.3 g of titanium dioxide and 2.1 g of purified talc in 72.6 g of water. Using a High Coated, the 3,000 tablets prepared above were coated with the coating solution to give film-coated tablets, each having 154.5 mg in weight.

EXAMPLE 162

Preparation of a Pharmaceutical Composition:
Liquid Inhalant

Formulation:

| Compound of the present invention | 400 μg |
| Physiological saline | 1 ml |

A 40 mg portion of the compound of the present invention was dissolved in 90 ml of physiological saline, and the solution was adjusted to a total volume of 100 ml with the same saline solution, dispensed in 1 ml portions into 1 ml capacity ampoule and then sterilized at 1151 for 30 minutes to give liquid inhalant.

EXAMPLE 163

Preparation of a Pharmaceutical Composition:
Powder Inhalant

Formulation:

| Compound of the present invention | 200 μg |
| Lactose | 4,000 μg |

A 20 g portion of the compound of the present invention was uniformly mixed with 400 g of lactose, and a 200 mg portion of the mixture was packed in a powder inhaler for exclusive use to produce a powder inhalant.

EXAMPLE 164

Preparation of a Pharmaceutical Composition:
Inhalation Aerosol

Formulation:

| Compound of the present invention | 200 μg |
| Dehydrated (Absolute) ethyl alcohol USP | 8,400 μg |
| 1,1,1,2-Tetrafluoroethane (HFC-134A) | 46,810 μg |

The active ingredient concentrate is prepared by dissolving 0.0480 g of the compound of the present invention in 2.0160 g of ethyl alcohol. The concentrate is added to an appropriate filling apparatus. The active ingredient concentrate is dispensed into aerosol container, the headspace of the container is purged with Nitrogen or HFC-134A vapor (purging ingredients should not contain more than 1 ppm oxygen) and is sealed with valve. 11.2344 g of HFC-134A propellant is then pressure filled into the sealed container.

The invention claimed is:

1. A compound which is 3(R)-1-phenethyl-(9[H]-xanthene-9-carbonyloxy)-1-azoniabicyclo[2.2.2] octane wherein an anion $X^-$ is associated with the positive charge of the nitrogen atom and wherein $X^-$ is a pharmaceutically acceptable anion of a mono- or polyvalent acid.

2. The compound according to claim 1 which is 3(R)-1-phenethyl-(9[H]-xanthene-9-carbonyloxy)-1-azoniabicyclo[2.2.2]octane bromide.

3. A pharmaceutical composition comprising a compound according to claim 1 in admixture with a pharmaceutically acceptable carrier or diluent.

4. The pharmaceutical composition of claim 3 comprising 3(R)-1-phenethyl-(9[H]-xanthene-9-carbonyloxy)-1-azoniabicyclo[2.2.2]octane bromide.

5. A method for treating chronic obstructive pulmonary disease, chronic bronchitis, bronchial hyperreactivity, asthma, or rhinitis which method comprises administering to a human or animal patient in need of such treatment an effective amount of a compound according to claim 1.

6. The method according to claim 5 comprising administering to the patient an effective amount 3(R)-1-phenethyl-(9[H]-xanthene-9-carbonyloxy)-1-azoniabicyclo[2.2.2]octane bromide.

* * * * *